(12) United States Patent
Sun et al.

(10) Patent No.: US 9,163,247 B2
(45) Date of Patent: Oct. 20, 2015

(54) VECTOR COMPRISING MANNOSE PROMOTER AND MANNOSE PROMOTER

(75) Inventors: Tianqi Sun, Heilongjiang (CN); Josef Altenbuchner, Nufringen (DE); Christoph Kiziak, Visp (CH)

(73) Assignee: Lonza AG, Visp (CH)

( * ) Notice: Subject to any disclaimer, the term of this patent is extended or adjusted under 35 U.S.C. 154(b) by 679 days.

(21) Appl. No.: 13/389,904

(22) PCT Filed: Aug. 2, 2010

(86) PCT No.: PCT/EP2010/061193
§ 371 (c)(1),
(2), (4) Date: Apr. 19, 2012

(87) PCT Pub. No.: WO2011/018376
PCT Pub. Date: Feb. 17, 2011

(65) Prior Publication Data
US 2012/0202246 A1    Aug. 9, 2012

(30) Foreign Application Priority Data

Aug. 10, 2009  (EP) .................................. 09010283

(51) Int. Cl.
| C07H 21/04 | (2006.01) |
| C12P 21/04 | (2006.01) |
| C12N 15/63 | (2006.01) |
| C12N 15/70 | (2006.01) |
| C12N 15/75 | (2006.01) |

(52) U.S. Cl.
CPC ................ C12N 15/63 (2013.01); C12N 15/70 (2013.01); C12N 15/75 (2013.01)

(58) Field of Classification Search
None
See application file for complete search history.

(56) References Cited

U.S. PATENT DOCUMENTS

2007/0259004 A1   11/2007  Schumann

FOREIGN PATENT DOCUMENTS

| DE | 10225380 A1 | 12/2003 |
| WO | 2004033633 A | 4/2004 |
| WO | 2006133210 A | 12/2006 |

OTHER PUBLICATIONS

Ming-Ming et al. Biotechnol. Lett. 28:1713-1718, 2006.*
Yamamoto et al., J. Bacteriol., 183(17):5110-5121, 2001.*
Tianki, Sun. "Regulation des Mannose-Operons in *Bacillus subtilis*, Dissertation zur Erlangung der Wurde eines Doctors in Naturwissenshaften." Internet citation, Apr. 16, 2010, pp. I-VI, XP002604428. Retrieved from Internet on Nov. 10, 2010: www.elib.uni-stuttgart.de/opus/volltexte/2010/5249/pdf/Regulation_des_Mannose_Operons.pdf.
Sun, Tianqui et al. "Characterization of a mannose utilization system in *Bacillus subtilis*." Journal of Bacteriology. American Society for Microbiology. Washington, DC. vol. 192, No. 8. Apr. 1, 2010. pp. 2128-2139, XP002604427, ISSN: 0021-9193, DOI: DOI: 10.1128/JB.01673-09.
Reizer Jonathan et al: "Novel phosphotransferase system genes revealed by genome analysis—the complete complement of PTS proteins encoded within the genome of *Bacillus subtilis*" Microbiology, Society for General Microbiology, Reading, GB, vol. 145, No. 12, Dec. 1, 1999, pp. 3419-3429, XP002326596, ISSN: 1350-0872.
Martin-Verstraete I et al: "The levanase operon of *Bacillus subtilis* expressed in *Escherichia coli* can substitute for the mannose permease in mannose uptake and bacteriophage lambda infection" Journal of Bacteriology Dec. 1996, vol. 178, No. 24, Dec. 1, 1996, pp. 7112-7119, XP002558890 ISSN: 0021-9193.
Kunst F. et al: "The complete genome sequence of the gram-positive bacterium *Bacillus subtilis*" Nature, Nature Publishing Group, London, UK, vol. 390, Nov. 20, 1997 (Jan. 1, 1997), pp. 249-266, XP002937517, ISSN: 0028-0836.
Stulke J. et al: "Regulation of carbon catabolism in *Bacillus* species" Annual Review of Microbiology 2000, vol. 54, Jan. 1, 2000, pp. 849-880, XP002558892, ISSN: 0066-4227.
Abranches, Jacqueline et al. "Characterization of *Streptococcus mutans* strains deficient in EIIAB Man of the sugar phosphotransferase system." Applied and Environmental Microbiology, American Society for Microbiology, US. vol. 69, No. 8. Aug. 1, 2003. pp. 4760-4769, XP002558891, ISSN: 0099-2240, DOI: DOI:10.1128/AEM.69.8.4760-4769.2003.
Juergen B. et al: "The stability of mRNA from the gsiB gene of *Bacillus subtilis* is dependent on the presence of a strong ribosome binding site" Molecular and General Genetics, vol. 258, No. 5, Jun. 1, 1998, pp. 538-545, XP002514867 Springer Verlag, Berlin, DE ISSN: 0026-8925.

* cited by examiner

*Primary Examiner* — Nancy T Vogel

(57) ABSTRACT

The present invention relates to a vector expressible in a prokaryotic host and a nucleic acid sequence comprising a mannose-inducible promoter of the mannose operon of *Bacillus subfiles* wherein the vector and nucleic acid sequence, respectively, can be suitably used for transforming a host cell for expression of a heterologous nucleic acid sequence coding a polypeptide in, in particular, high cell density fermentation.

25 Claims, 12 Drawing Sheets

```
TTTTATCTCA TTTGGATTAT TAAAAGCAGG GATTATTCCT TGCTTTTTTT
           ―――――――――→
              manR                                  -35
GTTATAGGGA AAAATGCCTT TATTACCGGA ACCTATGGTA AAAAAAGCGA
                         -10         +1  BglII
TTTTAATGAG CTGATTTCGG TATTTCAGTTG AGACAAGATC TTATTATTCA
  XbaI              AflII               NdeI
CACTTTCTAG AAATAATTTT CTTAAGAAGG AGATATACAT ATGACACATG
                                                  ――――→
                                                  LysA_Bs
```

Fig. 1

```
  |pSUN291▸             |pSUN384.1           |pSUN385.2
  |TGAATTTCTG CTGAATATAC ATT|ACATAGC AAACTCAAAG |AGTATAAAAA

|pSUN386.9 HindIII         -35
TCGCTTTTTT|CCGGAAGCTT CGGTAAAAAA CGAAACTTTT GTCTCTATGA PstI   -10      +1
TTTTGTTTTA TAATGTAAAC GGTTTCTTAT ATAGTATACT TATACTATCA
           >>...CRE..>>

AflII            NdeI
ATTTGCTCAA GTAGATACTG ACAGGCTTAA GAAGGAGATA TACATATGAC
                                                  ↘ lacZ
```

Fig. 3

```
       HindIII                  -35
TTTTTCCGGA AGCTTCGGTA AAAAACGAAA CTTTTTTTTC TATGATTTTG
     -10     CRE    +1
TTTTA TAATG TAAACGGTTT CTTATATAGT ATACTTATAC TATCAATTTG CTCAAGTAGA TACTGACAGG AAGGATAGAA AAACAGATGG AATACATAAA
                                              |―――→
                                              manR
```

Fig. 2

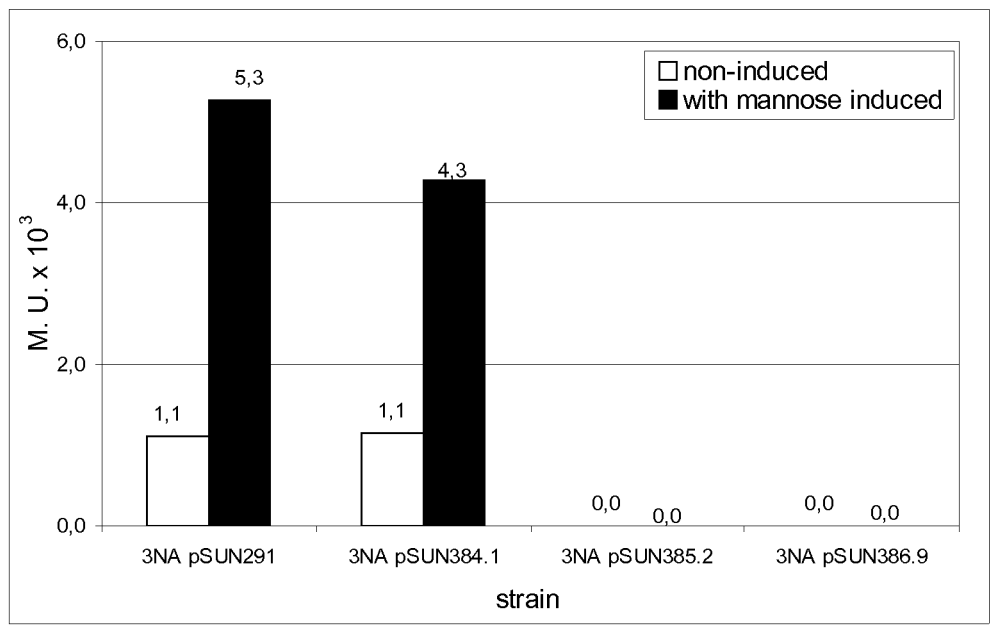
Fig. 8
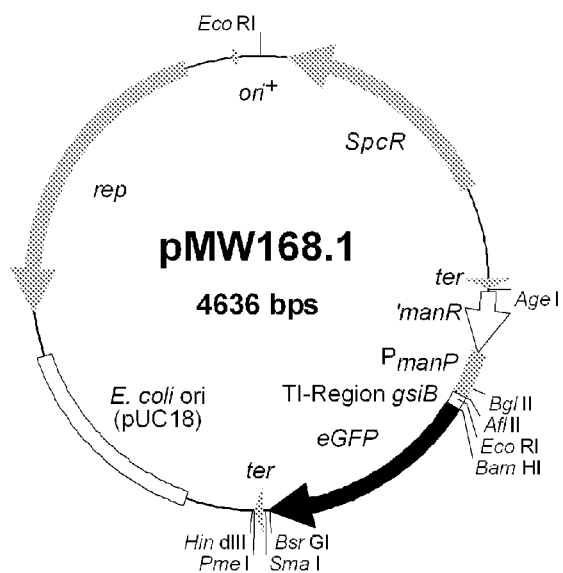
Fig. 9: plasmid map of pMW 168.1

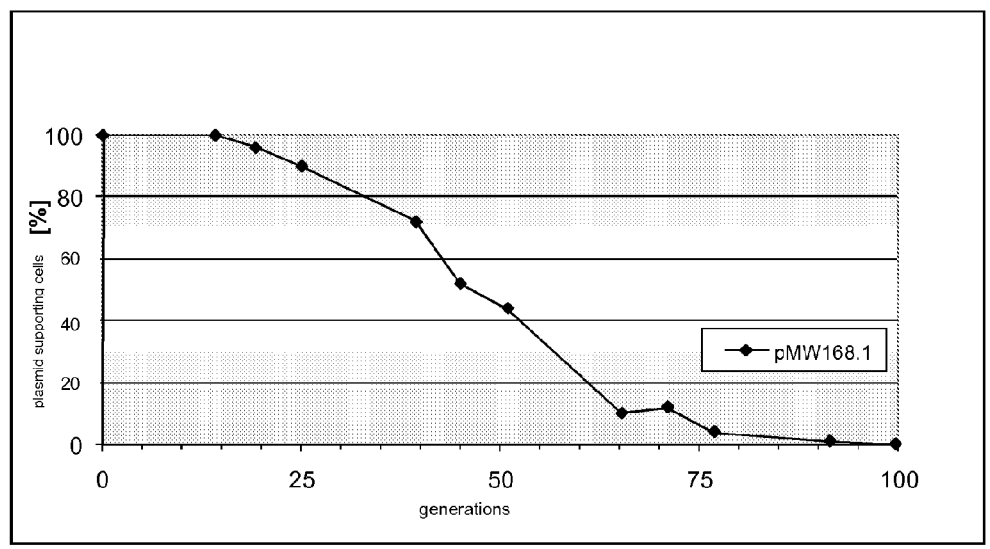
Fig. 10: plasmid stability test of pMW 168.1 in *B.subtilis* 3NA
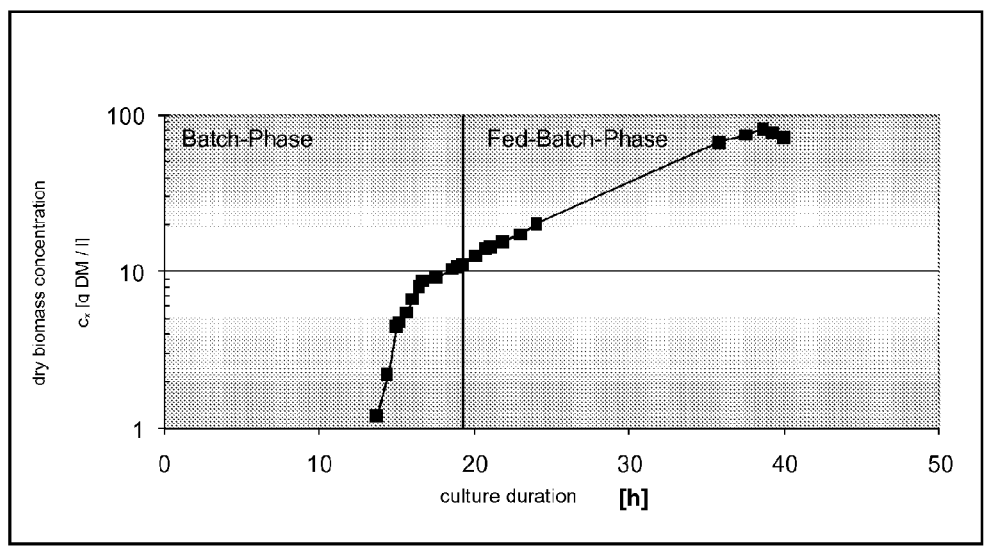
Fig. 11a: growth progress of run 1

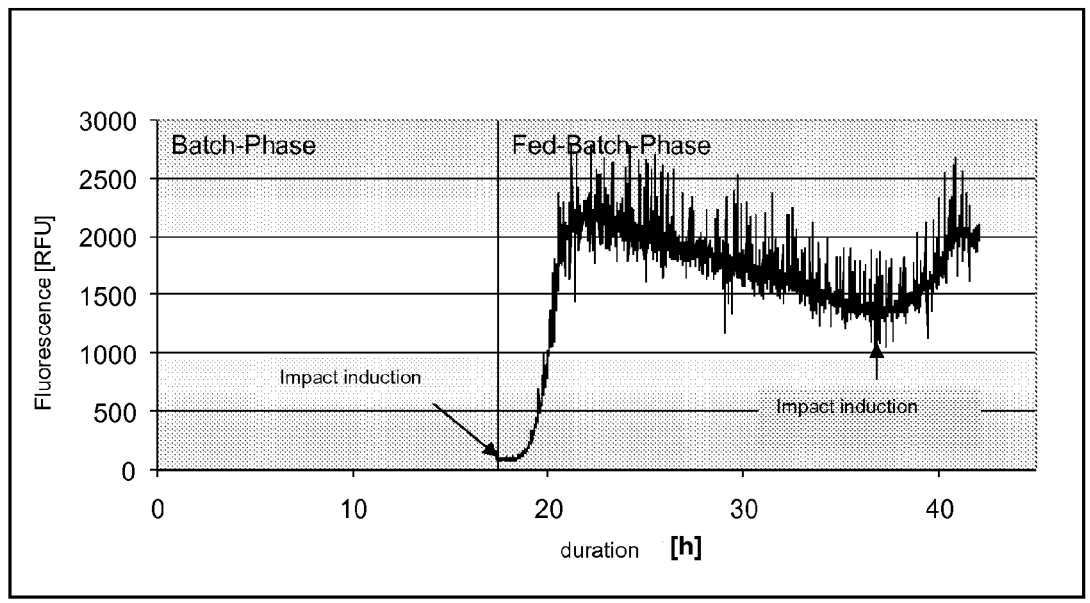
Fig. 11b: fluorescence signal of run 1
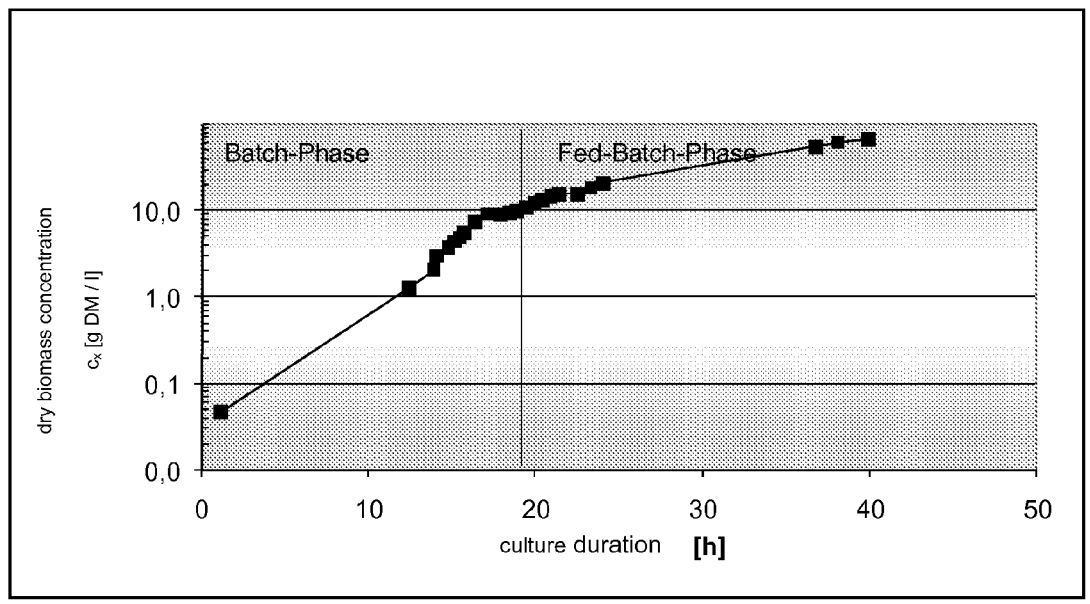
Fig. 12a: growth progress of run 2

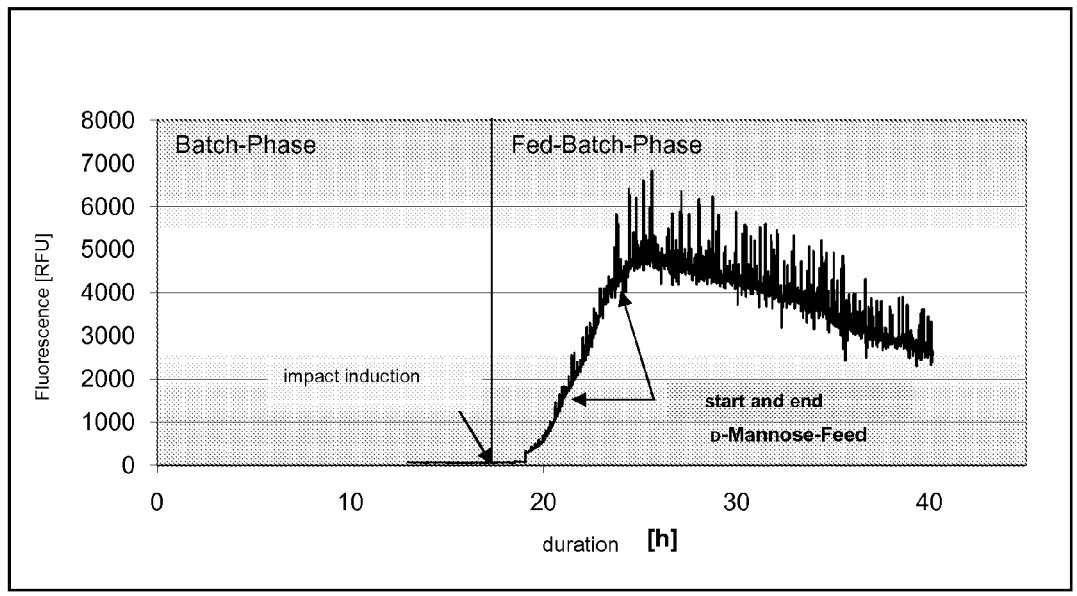
Fig. 12b: fluorescence signal of run 2
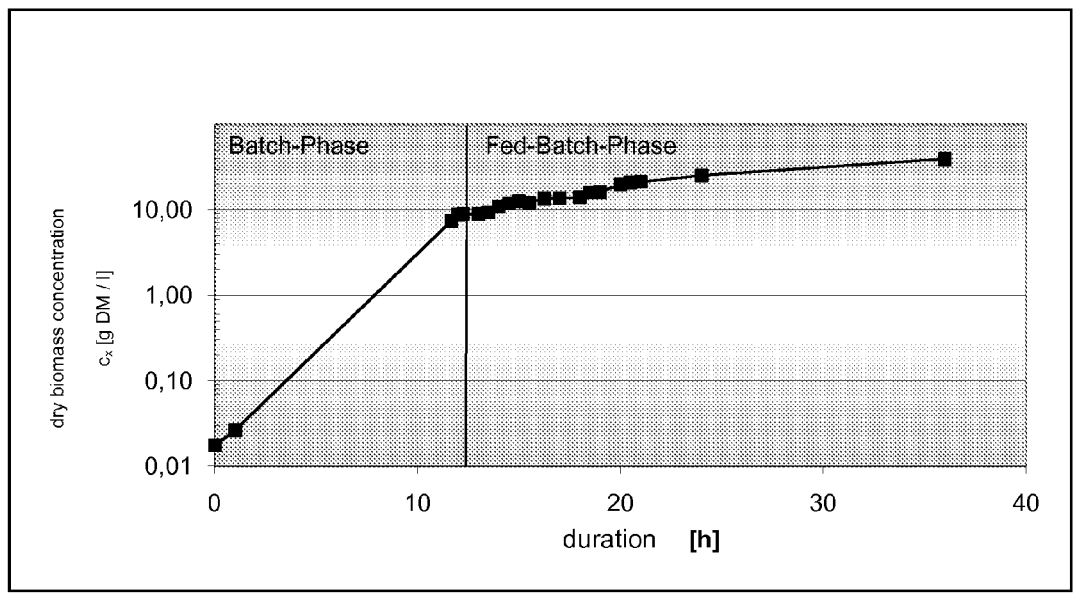
Fig. 13a: growth progress of run 3

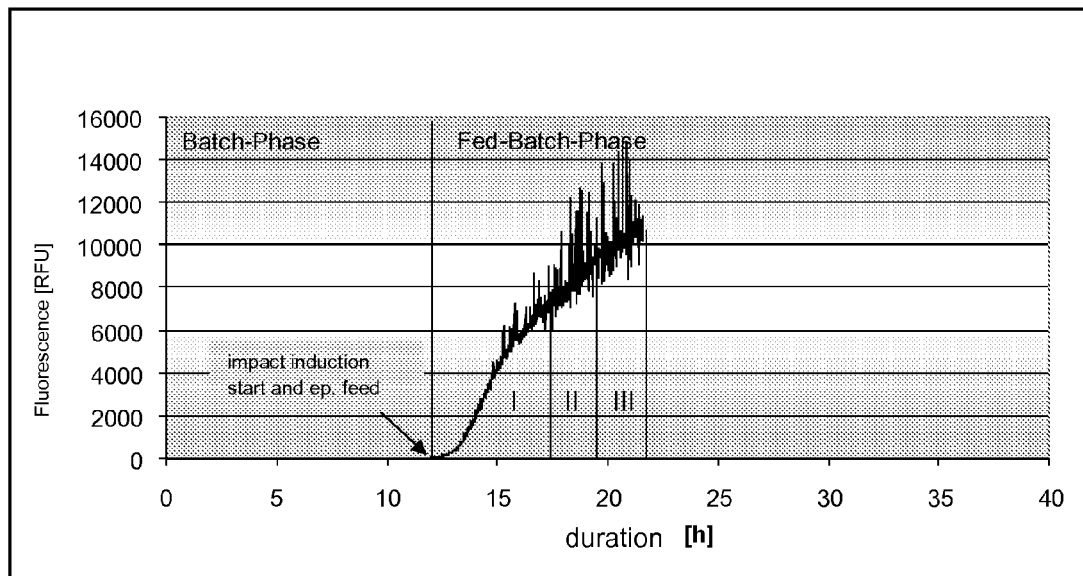
Fig. 13b: fluorescence signal of run 3
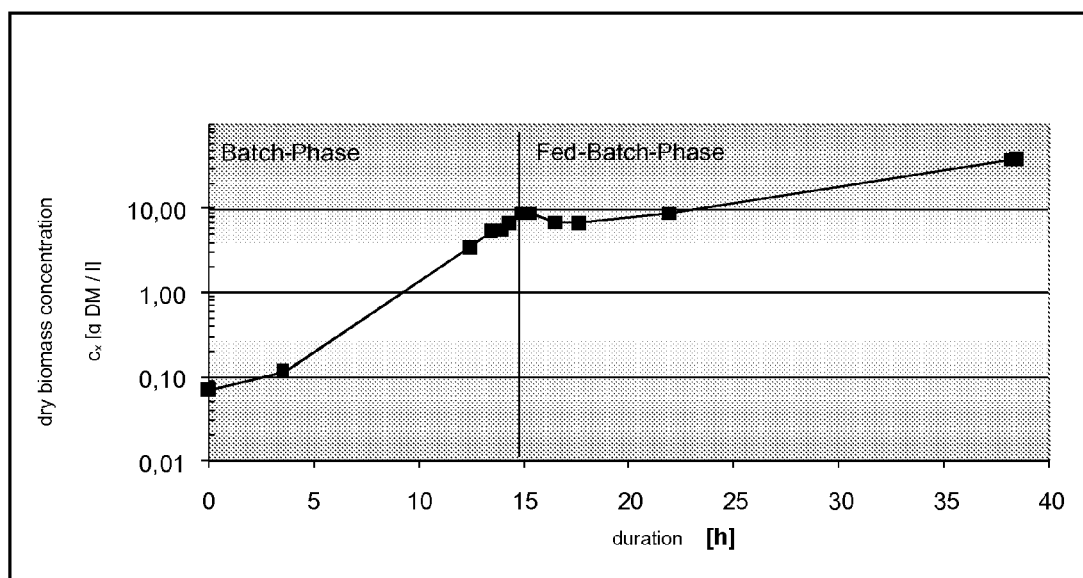
Fig. 14a: growth progress of run 4

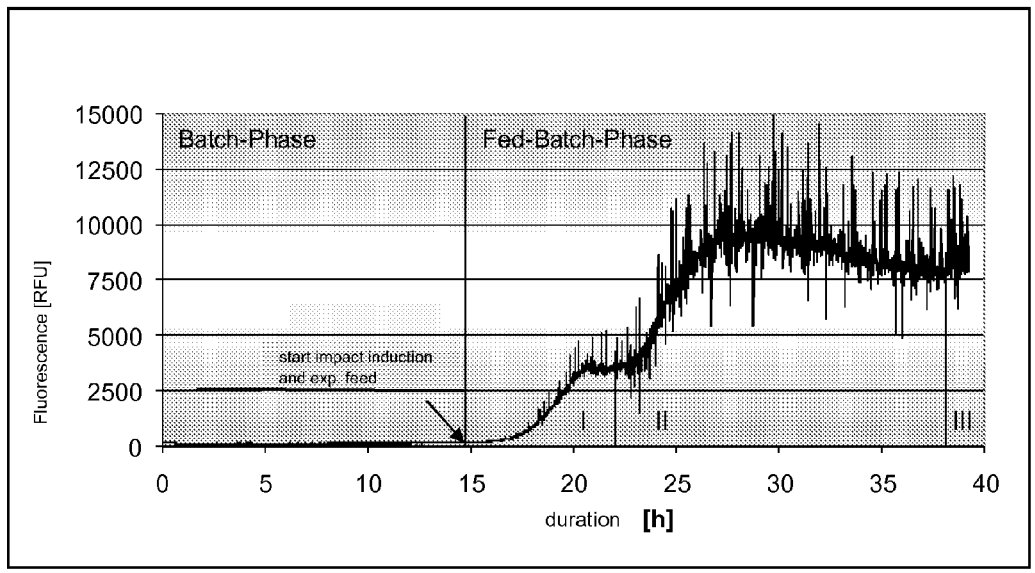
Fig. 14b: fluorescence signal of run 4
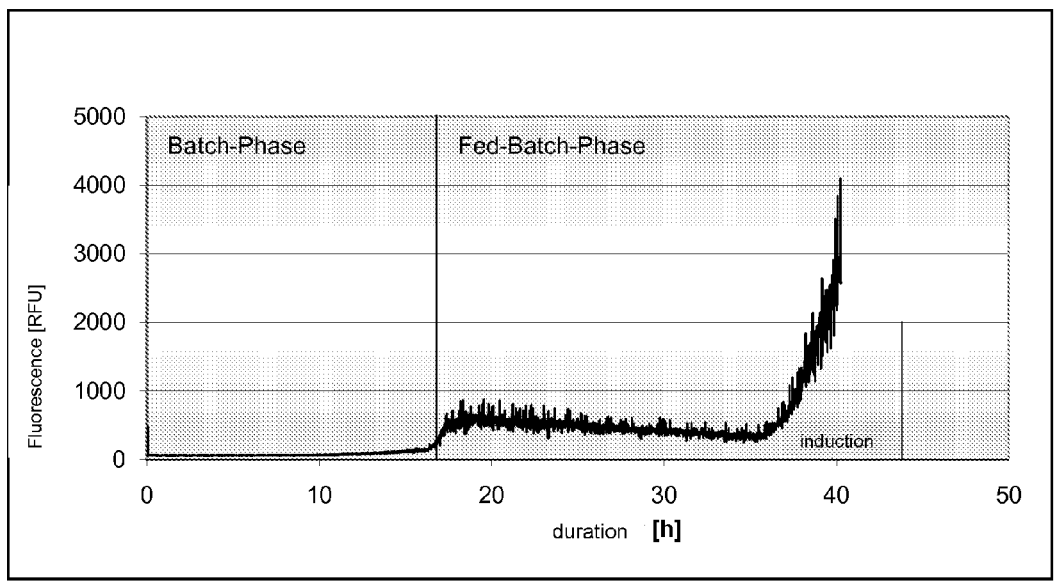
Fig. 15: fluorescence signal of run 5

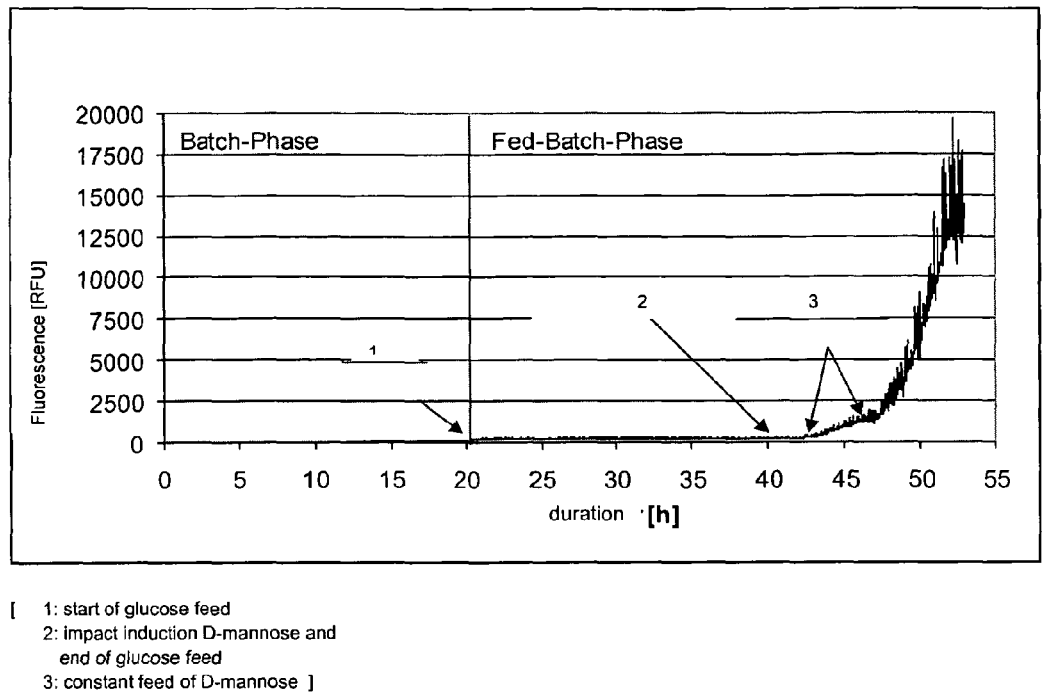
[  1: start of glucose feed
   2: impact induction D-mannose and
      end of glucose feed
   3: constant feed of D-mannose ]
Fig. 16: fluorescence signal of run 6
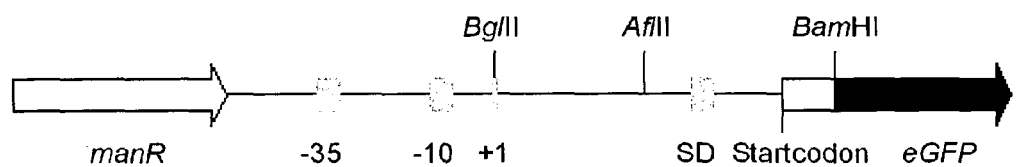
Fig. 17

SEQUENCE LISTING

```
<160> NUMBER OF SEQ ID NOS: 5

<210> SEQ ID NO 1
<211> LENGTH: 143
<212> TYPE: DNA
<213> ORGANISM: Bacillus subtilis

<400> SEQUENCE: 1
tagggaaaaa tgcctttatt accggaacct atggtaaaaa aagcgatttt aatgagctga      60
tttcggtata cagttgagac aagatcttat tattcacact ttctagaaat aattttctta     120
agaaggagat atacatatga cac                                             143

<210> SEQ ID NO 2
<211> LENGTH: 80
<212> TYPE: DNA
<213> ORGANISM: Bacillus subtilis

<400> SEQUENCE: 2
tagggaaaaa tgcctttatt accggaacct atggtaaaaa aagcgatttt aatgagctga      60
```

```
tttcggtata cagttgagac                                                    80

<210> SEQ ID NO 3
<211> LENGTH: 195
<212> TYPE: DNA
<213> ORGANISM: Bacillus subtilis

<400> SEQUENCE: 3
tgaatttctg ctgaatatac attacatagc aaactcaaag agtataaaaa tcgctttttt        60
ccggaagctt cggtaaaaaa cgaaactttt gtctctatga ttttgtttta taatgtaaac       120
ggtttcttat atagtatact tatactatca atttgctcaa gtagatactg acaggcttaa       180
gaaggagata tacat                                                       195

<210> SEQ ID NO 4
<211> LENGTH: 128
<212> TYPE: DNA
<213> ORGANISM: Bacillus subtilis

<400> SEQUENCE: 4
tgaatttctg ctgaatatac attacatagc aaactcaaag agtataaaaa tcgctttttt        60
ccggaagctt cggtaaaaaa cgaaactttt gtctctatga ttttgtttta taatgtaaac       120
ggtttctt                                                               128

<210> SEQ ID NO 5
<211> LENGTH: 121
<212> TYPE: DNA
<213> ORGANISM: Bacillus subtilis

<400> SEQUENCE: 5
tgaatttctg ctgaatatac attacatagc aaactcaaag agtataaaaa tcgctttttt        60
ccggaagctt cggtaaaaaa cgaaactttt gtctctatga ttttgtttta taatgtaaac       120
g                                                                      121
```

VECTOR COMPRISING MANNOSE PROMOTER AND MANNOSE PROMOTER

The present invention relates to vectors expressible in prokaryotic host cells comprising a mannose-inducible promoter for the heterologous expression of nucleic acids encoding, for example, for polypeptides such as recombinant proteins.

In particular, the present invention relates to new vectors for the heterologous expression in a host comprising a promoter region of the mannose operon operably linked to a transcriptional unit comprising a nucleic acid sequence which is heterologous to said host, whereas the expression of said nucleic acid sequence is controlled by said promoter region of the mannose operon. Further, the present invention relates to the use of these vectors for the heterologous expression of nucleic acids encoding for example polypeptides such as recombinant proteins.

Many systems have been described for the hetorologous expression of nucleic acids encoding, for example, for polypeptides (structural genes) in prokaryotic systems. To this, the host is transformed with a vector comprising the nucleic acid sequence of the structural gene of interest operably linked to a promoter which is a nucleic acid sequence that enables the structural gene to be transcribed. By suitable induction the promoter is activated and allows the transcription of the structural gene. Induction can be under negative or positive control.

In negative control induction a repressor is bound to the promoter and prevents the transcription of the structural gene. If a suitable inducer is present, the repressor is deactivated and transcription is allowed.

In positive control induction the promoter is activated upon binding of an activator, wherein binding of the activator to the promoter is mediated by a suitable inducer.

Typical inducers can be substrates which the prokaryotic hosts require for metabolism, for example, different types of sugars.

The present invention relates to positively inducible systems, wherein in the presence of a suitable substrate, i.e. inducer, an activator binds to the promoter which initiates transcription of the genes operably linked to said promoter.

Up to now, most heterologous gene expression systems in prokaryotic host systems have relied exclusively on a limited set of bacterial promoters. Consequently, also the number of substrates, which can be used as inducers, is limited as well.

Further, the yield of a heterologous expression system depends on the number of transformed prokaryotic hosts available. Thus, prokaryotic host systems are required that are able to grow to a high cell density, that is, allow fast proliferation without loosing the vector on cell division.

SUMMARY OF THE INVENTION

According to the present invention these and other objects as will be apparent from the following description have been achieved by providing new vectors comprising a promoter region of the mannose operon operably linked to a transcriptional unit comprising a nucleic acid sequence which is heterologous to said host, whereas the expression of said nucleic acid sequence is controlled by said promoter region of the mannose operon.

Also provided are the use of said new vector for the regulated heterologous expression of a nucleic acid sequence in a prokaryotic host; an isolated and purified nucleic acid sequence expressible in a host comprising a promoter region of the mannose operon; a prokaryotic host transformed with said vector or said isolated and purified nucleic acid sequence; a method for producing a polypeptide in a host using said vector or said isolated and purified nucleic acid sequence; as well as the use of a prokaryotic host transformed with said vector or said isolated and purified nucleic acid sequence in fermentation, in particular in high cell density fermentation.

Other objects and advantages will become apparent to those skilled in the art from review of the following detailed description with reference to the accompanying illustrative figures, and the attached claims.

BRIEF DESCRIPTION OF THE FIGURES

It is shown in

FIG. 1 the nucleic acid sequence from *B. subtilis* used in the mapping of the transcription initiation site of manP promoter with the transcription start site at an adenine nucleotide being highlighted, the deduced −35 and −10 boxes in italics, the end of manR and start of lys gene marked by arrows and the restriction sites BglII, XbaI, AflII and NdeI underlined; said sequence comprising SEQ ID Nos. 1 and 2;

FIG. 2 the nucleic acid sequence of the promoter region comprising manR promoter with the transcription start site at an guanine nucleotide being highlighted, the deduced −10 and −35 boxes being in italics, the start of the manR gene being indicated by an arrow and the HindIII restriction site and putative cre sequence being underlined;

FIG. 3 the nucleic acid sequence obtained from *B. subtilis* comprising the promoter region of manR promoter as contained in pSUN291, pSUN384.1 and pSUN385.2, respectively, with the start of lacZ being indicated by an arrow and the restriction sites being underlined; said sequence comprising SEQ ID Nos. 3, 4 and 5.

FIG. 8 the β-galactosidase activities of *B. subtilis* 3NA comprising the vectors pSUN291, pSUN384.1 and pSUN345.2 with the nucleic acid sequences as shown in FIG. 3;

FIG. 9 the plasmid map of expression vector pMW 168.1 according to the present invention;

FIG. 10 a diagram with the result of the plasmid stability test of pMW 168.1 in *B. subtilis* 3NA with the procental portion of cells containing the plasmid being plotted over the number of generations;

FIGS. 11 to 14 diagrams showing logarithmically the dry biomass concentration plotted over the duration of fermentation runs 1 to 4 and diagrams with the fluorescence signal (RFU) plotted over the duration of fermentation of fermentation runs 1 to 4; and FIGS. 15 and 16 the diagrams of the fluorescence signal plotted over the duration of fermentation of fermentation runs 5 and 6, FIG. 17 a schematical structure of the promoter-initiation recent as obtained in accordance to experiment 4a "construction of plasmid pMW 168.1;

DETAILED DESCRIPTION OF THE INVENTION

Figure 4:
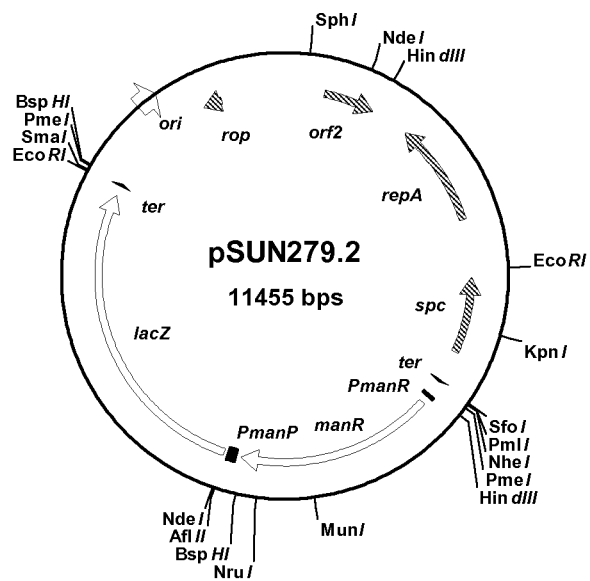
FIG. 4 the plasmid map of the expression vector pSUN 279.2 according to the present invention.

As used herein, the following definitions are supplied in order to facilitate the understanding of the present invention.

A "vector expressible in a host" or "expression vector" is a polynucleic acid construct, generated recombinantly or synthetically, with a series of specified polynucleic acid elements that permit transcription of a particular nucleic acid sequence in a host cell. Typically, this vector includes a transcriptional unit comprising a particular nucleic acid sequence to be transcribed operably linked to a promoter. A vector expressible in a host can be e.g. an autonomously or self-replicating plasmid, a cosmid, a phage, a virus or a retrovirus.

The terms "host", "host cell" and "recombinant host cell" are used interchangeably herein to indicate a prokaryotic cell into which one or more vectors or isolated and purified nucleic acid sequences of the invention have been introduced. It is understood that such terms refer not only to the particular subject cell but also to the progeny or potential progeny of such a cell. Because certain modifications may occur in succeeding generations due to either mutation or environmental influences, such progeny may not, in fact, be identical to the parent cell, but are still included within the scope of the term as used herein.

The term "comprise" is generally used in the sense of include, that is to say permitting the presence of one or more further features or components.

"Promoter" as used herein refers to a nucleic acid sequence that controls expression of a transcriptional unit. A "promoter region" is a regulatory region capable of binding RNA polymerase in a cell and initiating transcription of a downstream (3' direction) coding sequence. Within the promoter region will be found protein binding domains (consensus sequences) responsible for the binding of RNA polymerase such as the putative −35 box and the Pribnow box (−10 box). Further, the promoter region may comprise the transcription start site and binding sites for regulatory proteins.

"Mannose operon" refers to the mannose operon of *Bacillus subtilis*.

Three genes were identified in the mannose operon (Kunst F. N. et al., "The complete genome sequence of gram-positive bacterium *Bacillus subtilis*", Nature 390, pages 249 to 256 (1997)).

The first gene, manP, encodes a mannose specific enzyme component (transporter) that belongs to the fructose-permease family. The second gene, manA, encodes a mannose-6-phosphate isomerase whereas the function of the third gene, yjdF, is unknown. Upstream and in the same orientation of these three genes, a regulatory gene, manR, is located which codes for ManR, the activator of the mannose operon.

The mannose operon, consisting of the three genes manP-manA-yjdF (in the following jointly referred to as "manP"), is under the control of the manP promoter which itself is positively regulated. An other promoter, manR promoter, is responsible for the expression of manR that is essential for mannose-dependent induction of the manP promoter. The manR promoter region further comprises a catabolite regulator protein binding site (catabolite responsive element (cre)) of the manR gene.

"Cre sequence" refers to a nucleic acid sequence located upstream (5' direction) of catabolic genes. The cre sequence binds a catabolite control protein (CCP) preventing expression of the catabolic gene in carbon catabolite repression (CCR).

With "promoter regions of the mannose operon" are meant the promoter regions which regulate expression of manP as well as of manR with or without the cre sequence.

The "manP promoter" as referred to herein comprises at least of the −35 region, the Pribnow box, and the ManR binding site.

The "manR promoter" as referred to herein comprises at least of the putative −35 region, the Pribnow box, the ManR binding site and, optionally, a cre sequence.

D-mannose also referred to "mannose" is a 2-epimer of glucose and present in mannan and heteromannan polysaccharides, glycoproteins and numerous other glycoconjugates.

"CcpA" means "catabolite control protein A" which is a global regulator protein and can activate or represse the activation of some catabolic operons. In the case of the mannose operon CcpA plays a repressing role by binding to the cre sequence.

An "enhancer" is a nucleic acid sequence that acts to potentiate the transcription of a transcriptional unit independent of the identity of the transcriptional unit, the position of the sequence in relation to the transcriptional unit, or the orientation of the sequence. The vectors of the present invention optionally can include enhancers.

"Transcriptional unit" as used herein refers to a nucleic acid sequence that is normally transcribed into a single RNA molecule. The transcriptional unit might contain one gene (monocistronic) or two (dicistronic) or more genes (polycistronic) that code for functionally related polypeptide molecules.

A nucleic acid sequence is "operably linked" when it is placed into a functional relationship with another nucleic acid sequence. For example, a promotor is operably linked to a coding sequence if it affects the transcription of the sequence; or a transcription initiation region such as a ribosome binding site is operably linked to a nucleic acid sequence encoding e.g. a polypeptide if it is positioned so as to facilitate translation of the polypeptide. Linking can be accomplished by ligation at convenient restriction sites. If such sites do not exist, the synthetic oligonucleotide adaptors or linkers are used in accordance with conventional practice.

"Nucleic acid" or "nucleic acid sequence" or "isolated and purified nucleic acid or nucleic acid sequence" as referred in the present invention might be DNA, RNA, or DNA/RNA hybrid. In case the nucleic acid or the nucleic acid sequence is located on a vector it is usually DNA. DNA which is referred to herein can be any polydeoxynucleotide sequence, including, e.g. double-stranded DNA, single-stranded DNA, double-stranded DNA wherein one or both strands are composed of two or more fragments, double stranded DNA wherein one or both strands have an uninterrupted phosphodiester backbone, DNA containing one or more single-stranded portion(s) and one or more double stranded portion(s), double-stranded DNA wherein the DNA strands are fully complementary, double-stranded DNA wherein the DNA strands are only partially complementary, circular DNA, covalently-closed DNA, linear DNA, covalently cross-linked DNA, cDNA, chemicals-synthesized DNA, semi-synthetic DNA, biosynthetic DNA, naturally-isolated DNA, enzyme-digested DNA, sheared DNA, labeled DNA, such as radiolabeled DNA and fluorochrome-labeled DNA, DNA containing one or more non-naturally occurring species or nucleic acid. DNA sequences can be synthesized by standard chemical techniques, for example, the phosphotriester method or via automated synthesis methods and PCR methods. The purified and isolated DNA sequence may also be produced by enzymatic techniques.

RNA which is referred to herein can be e.g. single-stranded RNA, cRNA, double-stranded RNA, double-stranded RNA wherein one or both strands are composed of two or more fragments, double-stranded RNA wherein one or both strands have an uninterrupted phosphodiester backbone, RNA containing one or more single-stranded portion(s) and one or more double-stranded portion(s), double-stranded RNA wherein the RNA strands are fully complementary, double-stranded RNA wherein the RNA strands are only partially complementary, covalently crosslinked RNA, enzyme-digested RNA, sheared RNA, mRNA, chemically-synthesized RNA, semi-synthetic RNA, biosynthetic RNA, naturally-isolated RNA, labeled RNA, such as radiolabeled RNA and fluorochrome-labeled RNA, RNA containing one or more non-naturally-occurring species of nucleic acid.

With "variants" or "variants of a sequence" is meant a nucleic acid sequence that varies from the reference sequence by conservative nucleic acid substitutions, whereby one or more nucleic acids are substituted by another with same characteristics. Variants encompass as well degenerated sequences, sequences with deletions and insertions, as long as such modified sequences exhibit the same function (functionally equivalent) as the reference sequence.

As used herein, the terms "polypeptide", "peptide", "protein", "polypeptidic" and "peptidic" are used interchangeably to designate a series of amino acid residues connected to the other by peptide bonds between the alpha-amino and carboxy groups of adjacent residues.

The term "isolated and purified nucleic acid sequence" refers to the state in which the nucleic acid sequence will be in accordance with the present invention. The nucleic acid sequence will be free or substantially free of material with which they are naturally associated such as other nucleic acids with which they are found in their natural environment, or the environment in which they are prepared (e.g. cell culture) when such preparation is by recombinant technology practiced in vitro or in vivo.

The terms "transformation", "transformed" or "introducing a nucleic acid into a host cell" denote any process wherein an extracellular nucleic acid like a vector, with or without accompanying material, enters a host cell. The term "cell transformed" or "transformed cell" means the cell or its progeny into which the extracellular nucleic acid has been introduced and thus harbours the extracellular nucleic acid. The nucleic acid might be introduced into the cell so that the nucleic acid is replicable either as a chromosomal integrant or as an extra chromosomal element. Transformation of appropriate host cells with e.g. an expression vector can be accomplished by well known methods such as microinjection, electroporation, particle bombardement or by chemical methods such as Calcium phosphate-mediated transformation, described e.g. in Maniatis et al. 1982, Molecular Cloning, A laboratory Manual, Cold Spring Harbor Laboratory or in Ausubel et al. 1994, Current protocols in molecular biology, John Wiley and Sons.

"Heterologous nucleic acid sequence" or "nucleic acid sequence heterologous to a host" means a nucleic acid sequence which encodes e.g. an expression product such as a polypeptide that is foreign to the host ("heterologous expression" or "heterologous product") i.e. a nucleic acid sequence originating from a donor different from the host or a chemically synthesized nucleic acid sequence which encodes e.g. an expression product such as a polypeptide that is foreign to the host. In case the host is a particular prokaryotic species, the heterologous nucleic acid sequence is preferably originated from a different genus or family, more preferred from a different order or class, in particular from a different phylum (division) and most particular from a different domain (empire) of organisms.

The heterologous nucleic acid sequence originating from a donor different from the host can be modified, before it is introduced into a host cell, by mutations, insertions, deletions or substitutions or single nucleic acids or a part of the heterologous nucleic acid sequence as long as such modified sequences exhibit the same function (functionally equivalent) as the reference sequence. A heterologous nucleic acid sequence as referred herein encompasses as well nucleic sequences originating from a different domain (empire) of organisms such as from eukaryotes (of eukaryotic origin) such as e.g. human antibodies which have been used in phage display libraries and of which single nucleic acids or a part of the nucleic acid sequences have been modified according to the "codon usage" of a prokaryotic host.

Within the meaning of the present invention the term "heterologous nucleic acid sequence" or "nucleic acid sequence heterologous to a host" encompasses also a nucleic acid sequence which is derived from the host and encodes for a polypeptide, naturally expressed in that host, wherein the nucleic acid sequence is inserted into a vector of the present invention and under control of the promoter region of mannose operon of the present invention.

"Transcription initiation region" is a signal region which promotes transcription initiation and which comprises the sequence for the ribosome binding site such as the Shine Dalgarno sequence. Typically the transcription initiation region is located downstream to the transcription initiation site and is operably linked to the genes to be expressed.

"Transcription termination region" refers to a sequence which causes RNA polymerase to terminate transcription. The transcription termination region is usually part of a transcriptional unit which can avoid unwanted transcription of other nearby genes or transcription form other potential promoters and can increase the stability of the mRNA.

"Antibody" refers to a class of plasma proteins produced by the B-cells of the immune system after stimulation by an antigen. Mammal (i.e. Human) antibodies are immunoglobulins of the Ig G, M, A, E or D class. The term "antibody" as used for the purposes of this invention includes, but is not limited to, polyclonal antibodies, monoclonal antibodies, anti-idiotypic antibodies and aut-antibodies present in autoimmune diseases, such as diabetes, multiple sclerosis and rheumatoid arthritis as well as chimeric antibodies.

In one aspect, the present invention provides a vector expressible in a host comprising a promoter region of the mannose operon operably linked to a transcriptional unit comprising a nucleic acid sequence which is heterologous to that host, whereas the expression of said nucleic acid sequence is controlled by said promoter region of the mannose operon.

The vector according to the invention is preferably an autonomously or self-replicating plasmid, a cosmid, a phage, a virus or a retrovirus. A wide variety of host/vector combinations may be employed in expressing the nucleic acid sequences of this invention. Useful expression vectors, for example, may consist of segments of chromosomal, non-chromosomal and/or synthetic nucleic acid sequences. Suitable vectors include vectors with specific host range such as vectors specific for e.g. *B. subtilis* and *E. coli*, respectively as well as vectors with broad-host-range such as vectors useful for gram-positive bacteria and gram-negative bacteria. "Low-copy", "medium-copy" as well as "high-copy" plasmids can be used.

For example, in *Bacillus subtilis* a low copy plasmid is pAMbeta1, medium copy plasmids are pBS72 derivatives and a high copy plasmid is pUB110.

According to the present invention the promoter region of the mannose operon comprises the manR promoter region and the manP promoter region, respectively.

The nucleic acid sequence from *B. subtilis* encompassing the C-terminal end of manR, the intergenic region between manR and manP, followed by the lysostaphin gene lys as reporter gene, is given in FIG. 1.

The nucleic acid sequence of the present invention comprising the promoter region of manP preferably comprises the nucleic acid sequence of FIG. 1 from by −80 to the start codon of lys (SEQ ID NO. 1) and more preferably the nucleic acid sequence of FIG. 1 from by −80 and inclusive by −1, i.e. upstream of the transcription initiation site A at bp+1 (SEQ ID No. 2).

The nucleic acid sequence from *B. subtilis* encompassing the promoter region of manR, the transcription initiation site G at bp+1, a putative cre sequence, the transcription initiation region between bp+1 and manR, as well as part of manR, is given in FIG. 2 and in FIG. 3, wherein manR is replaced by lacZ. The nucleic acid sequence of the present invention comprising the promoter region of manR preferably comprises the nucleic acid sequence of FIG. 3 from by −122 to the start codon of lacZ (SEQ ID NO. 3), more preferably, the nucleic acid sequence of FIG. 3 from by −122 and by +7, i.e. inclusive the putative cre-sequence, (SEQ ID NO. 4), and, in particular, the nucleic acid sequence of FIG. 3 from by −122 and bp−1, i.e. upstream of the transcription inition site G at via the phosphoenolpyruvate: carbonhydrate phosphotransferase system (PTS). In the PTS, the respective hexose is simultaneously phosphorylated and transported into the cell during up-take. Uptake and utilization of a specific sugar substrate is subject to carbon catabolite repression (CCR). In the presence of glucose, the preferred sugar substrate of *B. subtilis*, transcription of the genes for uptake and utilization of other substrates such as the mannose operon, is repressed. The mechanism of the glucose dependent CCR in *B. subtilis* has been widely studied and is known in the art (Stülke J. et al., "Regulation of carbon catabolism in *Bacillus* species", in Annu. Rev. Microbiol. 54, 2000, pages 849-880)

The transcriptional unit according to the present invention usually further comprises a translation initiation region upstream of the initiation point (start codon) of the translation of said transcriptional unit, whereas the translation initiation region is operably linked to the nucleic acid sequence. The translation initiation region is usually located upstream directly adjacent to the initiation point of the translation of the transcriptional unit which can be ATG, GTG or TTG.

The translation initiation region can be the translation initiation region of the transcriptional unit of manP gene or manR gene in the mannose operon.

The translation initiation region of manP or manR gene of the mannose operon can be partially or totally replaced by an other translation initiation region.

For example, the translation initiation regions of tufA (elongation factor Tu) and gsiB (stress protein; Jürgen et al., 1998, Mol. Gen. Genet. 258, 538-545) both from *B. subtiliis*, can be used.

The respective nucleic acid sequences of tufA and gsiB are shown below with the start codon in bold type, the restriction sites underlined and the Shine-Dalgarno-Sequence highlighted.

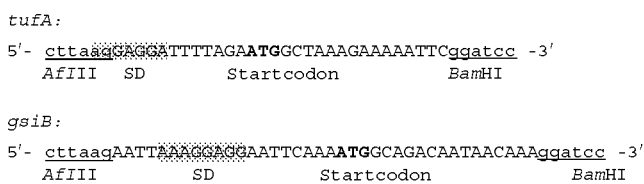

pb+1 (SEQ ID NO. 5). Both the promoter regions of manP and manR comprise binding sites for ManR. The present invention also encompasses a sequence complementary to any of the SEQ ID NOs. 1-5 and variants thereof.

The promoter regions of the mannose operon, such as the manP promoter region, the manR promoter region (with or without cre sequence) as well as the promoter regions in accordance to the sequences SEQ ID NOs. 1-5, a sequence complementary thereof or variants thereof used in the present invention are usually from the mannose operon of *B. subtilis* or from a functional equivalent promoter region of other prokaryotic organisms, in particular of organisms of the family of bacilaceae. A functional equivalent promoter region of other prokaryotic organisms encompass a promoter region which is inducible by D-mannose, i.e. a promoter region having a higher expression activity in the presence than in the absence of mannose.

In many prokaryotic organisms such as Firmicutes like *B. subtilis*, the mannose operon is involved in the metabolism of D-mannose.

*B. subtilis* can use many different sugars as carbon source. Hexoses such as glucose and D-mannose are mainly taken up By suitable selection of the transcription initiation region the stability of the mRNA can be enhanced, which is an important feature in gene expression. The stability of the mRNA is characterized by its specific half life.

In addition to the transcription initiation region also the initiation point of the translation as well as, optionally, a number of the codons of the gene following the initiation point, for example about 5-6 codons, can be replaced, for example as shown above in the nucleic acid sequences of tufA and gsiB, respectively.

The translation initiation region can further comprise a sequence encoding signal sequence operably linked to the heterologous nucleic acid sequence of the invention. The signal sequence is usually located downstream directly adjacent to the initiation point of the translation, which can be ATG, GTG or TTG of the transcriptional unit. In case a dicistronic or polycistronic transcriptional unit is used, different or identical signal sequences operably linked to each of the cistrons can be applied. Preferably different signal sequences are used in such a case. The signal sequence used can be a prokaryotic or an eukaryotic signal sequence. Usually prokaryotic signal sequences are applied.

The DNA sequences encoding signal sequences to be employed in the expression vectors of the present invention can be obtained commercially or synthesized chemically. For example, signal sequences can be synthesized according to the solid phase phosphoramidite trimester method described, e.g. in Beaucage & Caruthers, 1981, Tetrahedron LeHs. 22, 1859-1862 as described in Van Devanter et. Al., Nucleic Acids Res. 12:6159-6168 (1984). Purification of oligonucleotides can be performed by either native acrylamide gel electrophoresis or by anion-exchange HPLC as described in Pearson & Reanier, J. Chrom. 255:137-149 (1983).

Usually the transcriptional unit further comprises a transcription termination region. Preferably strong transcription termination regions are used for avoiding "reading through" by the promoter out of the transcription unit into the flanking plasmid sequence as well as from other plasmid promoters into the transcription unit. Further, stabilization of the mRNA was observed in the presence of such transcription termination region. A suitable example for a strong transcription termination region has the nucleic acid sequence 5'-CGAGACCCCTGTGGGTCTCG-3' from the 3'-region of tufA from B. subtilis 168 which is commercially available.

The heterologous nucleic acid sequence according to the present invention encodes an expression product that is foreign to the host. In case the host is a prokaryotic species such as B. subtilis or E. coli the nucleic acid sequence of interest can be more preferably from another class like the gamma-proteobacteria such as from e.g. Burkholderia sp., in particular from a different phylum such as archae bacteria, in most particular from an eukaryotic organism such as mammals in particular from humans. However, the heterologous nucleic acid sequence might be modified according to the "codon usage" of the host. The heterologous sequence according to the present invention is usually a gene of interest. The gene of interest preferably encloses a heterologous polypeptide such as a structural, regulatory or therapeutic protein, or N- or C-terminal fusions of structural, regulatory or therapeutic protein with other proteins ("Tags") such as green fluorescent protein or other fusion proteins. The heterologous nucleic acid sequence might encode as well a transcript which can be used in the form of RNA, such as e.g. antisense-RNA. The protein may be produced as an insoluble aggregate or as a soluble protein which is present in the cytoplasm or in the periplasmic space of the host cell, and/or in the extracellular medium. Preferably, the protein is produced as a soluble protein which is present in the periplasmic space of the host cell and/or in the extracellular medium.

The heterologous protein of interest can be of human, mammalian or prokaryotic origin. Other proteins are antigens, such as glycoproteins and carbohydrates from microbial pathogens, both viral and antibacterial, and from tumors. Other proteins are enzymes like chymosin, proteases, polymerases, dehydrogenases, nucleases, glucanases, oxidases, alpha-amylases, oxidoreductases, lipases, amidases, nitril hydratases, esterases or nitrilases.

In the present invention the order and the distance in which the signal sequence and the heterologous nucleic acid sequences are arranged within the expression vectors can be varied. In preferred embodiments the signal sequence is 5'(upstream) to the nucleic acid sequence encoding e.g. the polypeptide of interest. The signal sequence and the nucleic acid sequence encoding e.g. the polypeptide of interest can be separated by zero to about 1000 amino acids. In preferred embodiments, the signal sequence and nucleic acid sequence encoding e.g. the polypeptide of interest are directly adjacent to each other, i.e. separated by zero nucleic acids.

Preferably, the vector of the present invention comprises a nucleic acid sequence in accordance of any of the sequences SEQ ID NOs 1-5 a sequence complementary thereof and variants thereof.

Also encompassed by the present invention is the use of a vector according to the invention for the regulated heterologous expression of a nucleic acid sequence in a prokaryotic host.

Expression is started by addition of a suitable inducer. The inducer of the mannose operon is mannose or a derivate thereof capable to induce the manR promoter region or manP promoter region of the mannose operon. The expression can be regulated by the amount of inducer available to the prokaryotic host.

In still another aspect the invention provides an isolated and purified nucleic acid sequence comprising a promoter region of the mannose operon. Preferably, the isolated and purified nucleic acid sequence comprises the manP promoter and/or the manR promoter of the mannose operon. More preferably, the isolated and purified nucleic acid sequence comprises any of the SEQ ID NOs 1 to 5. The isolated and purified nucleic acid sequence comprising a promoter region of the mannose operon can be operably linked to a transcriptional unit comprising a nucleic acid sequence encoding for a polypeptide, wherein the expression of the nucleic acid sequence encoding for the polypeptide is under control of the promoter region of the mannose operon. The isolated and purified nucleic acid sequence according to the present invention may comprise the complete or a partial sequence of the regulatory gene manR. At least the isolated and purified nucleic acid sequence of the manR promoter may comprise a cre sequence.

The isolated and purified nucleic acid sequence of this invention can be isolated according to standard PCR protocols and methods well known in the art. The purified and isolated DNA sequence can further comprise one or more regulatory sequences, as known in the art, e.g. an enhancer, usually employed for the expression of the product encoded by the nucleic acid sequence.

In order to select host cells successfully and stably transformed with the vector or the isolated and purified nucleic acid sequence of the present invention, a gene that encodes a selectable marker (e.g. resistance to antibiotics) can be introduced into the host cells along with the nucleic acid sequence of interest. The gene that encodes a selectable marker might be located on the vector or on the isolated and purified nucleic acid sequence or might optionally be co-introduced in a separate form, e.g. on a separate vector. Various selectable markers can be used including those that confer resistance to antibiotics, such as spectinomycin, hygromycin, ampicillin and tetracyclin. The amount of the antibiotic can be adapted as desired in order to create selective conditions. Usually one selectable marker is used.

In case that the vector is a shuttle vector a marker common to the suitable hosts may be selected. For example, in case that the vector is a shuttle vector replicable in both E. coli and B. subtilis the resistance marker gene encoding the spectinomycin-adenyltransferase of Enterococcus faecalis can be used which confers resistance to spectinomycin.

As well reporter genes such as fluorescent proteins can be introduced into the host cells along with the nucleic acid sequence of interest, in order to determine the efficiency of transformation. Suitable reporter genes are, for example, those coding for enhanced green fluorescent protein (eGFP) and lacZ encoding for β-galactosidase. Both reporter genes are commercially available and are widely used.

Another aspect to the present invention is to provide a prokaryotic host transformed with a vector of the present invention wherein the vector comprises a promoter region of the mannose operon. Preferably the vector comprises any of the SEQ ID NOs 1 to 5, a sequence complementary thereof or variants thereof.

A wide variety of prokaryotic host cells are useful to be transformed with a mannose-inducible promoter region of the mannose operon according to the present invention. These hosts may include strains of Gram-positive cells such as *Bacillus* and *Streptomyces*, or Gram-negative cells such as *E. coli* and *Pseudomonas*. Preferably, the host cell is a Gram-positive cell, in particular of phylum Firmicutes, more preferably the host cell is *Bacillus*.

*Bacillus* which can be used are e.g. the strains *B. subtilis*, *B. amyloliquefaciens*, *B. lichenifonnis*, *B. natto*, *B. megaterium*, etc. Preferably, the host cell is *B. subtilis*, such as *B. subtilis* 3NA and *B. subtilis* 168.

*E. coli* which can be used are e.g. the strains TG1, W3110, DH1, XL1-Blue and Origami, which are commercially available.

Suitable host cells are commercial available, for example, from culture collections such as the DSMZ (Deutsche Sammlung von Mikroorganismen and Zellkulturen GmbH, Braunschweig, Germany). For example, *Bacillus* is obtainable from the *Bacillus* Genetic Stock Center.

The host cell might or might not metabolize mannose. A host cell which is ordinarily capable to uptake and metabolize mannose like *B. subtilis* might be modified to be deficient in one or more functions related to the uptake and/or metabolism of mannose. Deficiency in one or more functions related to the uptake and/or metabolism of mannose can be achieved by e.g. suppressing or blocking the expression of a gene coding for a protein such as the manA gene coding for mannose-6-phosphat-isomerase. This can be done by known technique such as transposon supported mutagenesis or knock-out mutation.

Usually, the prokaryotic host corresponds to the signal sequences chosen, for example in case signal sequences of *Bacillus* are used, the host cell is usually a member of the same family of the bacillacea, more preferably the host cell is a *Bacillus* strain.

Preferably a host is used which possesses a phosphoenolpyruvate: carbohydrate phosphotransferase system (PTS). In particular, the host possessing a PTS system is a microorganism of the order Bacillales, in particular of genus *Bacillus* and more preferably of species *Bacillus subtilis* or a microorganism of the order Enterobacteriales, preferably of the genus *Escherichia* and more preferably of species *E. coli*.

The primary element of CCR is the catabolite control protein A (CcpA), which is capable to bind to the cre-sequence, such as the putative cre sequence in SEQ ID NOs 3 and 4. In the bound state of CcpA transcription of the respective gene, here manR, is repressed. In absence of glucose and in presence of an inducer such as D-mannose, there is no repression by binding of CcpA and the transcription of the genes of the mannose operon are initiated by binding of the regulatory protein (ManR) to the respective binding sites of the promotor regions of the mannose operon.

Surprisingly it was found by the present inventors, that ManR is not only the regulatory protein for the manP promoter region but an autoregulator for manR itself.

Further provided with the present invention is a method for producing a polypeptide in a host cell, comprising the steps of
a) constructing a vector,
b) transforming a prokaryotic host with said vector,
c) allowing expression of said polypeptide in a cell culture system under suitable conditions,
d) recovering said polypeptide from the cell culture system.

The vector used, as well as its construction and the transformation of a prokaryotic host are as defined above, whereas the heterologous nucleic acid sequence comprised by the vector encodes a polypeptide.

As cell culture system continuous or discontinuous culture such as batch culture or fed batch culture can be applied in culture tubes, shake flasks or bacterial fermentors.

For culturing the host cells conventional media as known in the art can be used such as complex media like "nutrient yeast broth medium", a glycerol containing medium as described by Kortz et al. 1995, J. Biotechnol. 39, 59-65, a mineral salt media as described by Kulla et al., 1983, Arch. Microbiol, 135, 1, a batch medium for *E. coli* fermentation as described by Wilms et al., 2001, Biotechnol. Bioeng. 73, 95-103 or LB-medium as described by Bertram et al, 1051, J. Bacteriol. 62, 293-300.

The medium comprises a suitable carbon source, for example as sugar such as glucose, as a substrate for the host cell to be grown. The carbon source used as substrate is different from the inducer.

The medium might be modified as appropriate, e.g. by adding further ingredients such as buffers, salts, vitamins, amino acids, antibiotics or other micronutrients as are generally known to those of skill in the art. As well different media or combinations of media can be used during the culturing of the cells. Preferably, the medium used as basic medium should not include the inducer, in order to achieve a tight regulation of the mannose promoter regions.

Addition of the inducer can be started after the culture reaches a determining parameter. Examples for such determining parameters are the optical density (OD) indicating the cell concentration of the culture, or concentration of carbon source, which is different from the inducer.

For example, in the present process the inducer can be added after the culture reaches in appropriate OD depending on the specific culture system. For batch culture in shaking flasks a typical $OD_{600}$ as determining parameter is about 0.3 or higher.

Usually, the amount of inducer, such as mannose, in the medium of the culture of prokaryotic host is adjusted to be about 10 g/l, preferably about 5 g/l, more preferably about 2 g/l. However, the amount of inducer added can be adapted on the requirements of a specific fermentation process.

The mode of addition of inducer (induction regime) can be selected according to the specific culture system. By the mode of addition growth rate and expression rate of the host cells can be further regulated. For example, mannose can be added discontinuously or continuously over suitable time periods. In discontinuous mode (impact induction) addition can be once at the induction point only, or twice or even several times in suitable intervals. The suitable mode depends on the culture system and can be readily determined by those skilled in the art. For example, in continuous mode, mannose can be added in a constant rate or decreasing/increasing rate. Continuous addition can be further within a selected time interval of the culture, for example selected time interval during exponential growth of the culture.

Further, a combination of discontinuous and continuous induction regime is possible.

According to an embodiment of fed batch culture of the present invention in the batch phase the cells are grown to a cell density of between 20 to 30 $OD_{600}$ and, then, the cultivation is switched to fed phase with addition of a mixture of primary carbon source and mannose. In the fed phase the ratio of primary carbon source to mannose can be varied, suitable ratios are from 3:1 to 1:3. By variation of the ratio primary carbon source:mannose, the expression rate can be controlled.

Appropriate pH ranges are, e.g., 6-8 preferably 7-7.5, appropriate culture temperatures are between 10 and 40° C., preferably between 30 and 37° C.

The cells are incubated usually as long as it takes until the maximum amount of expressed product and/or biomass has accumulated, preferably between 1 hour and 20 days, more preferably between 5 hours and 3 days.

As the yield of biomass the amount of expressed product depends on the culture system used. In shake flask culture usually expressed product in the amount of 0.5 g/l culture medium can be produced with a host transformed with a vector of the present invention. Using a fermentor culture in a batch and/or fed-batch mode expressed product in the amount of usually more than 0.5 g/l fermentation broth, preferably more than 1 g/l, more preferably more than 1.3 g/l can be obtained.

Further, in the fermentation process of that present invention using the host cells of the present invention high cell densities can be obtained from at least 10 to 30 $OD_{600}$, in particular at least 50 $OD_{600}$, preferably about 250 $OD_{600}$ or more, more preferably at least 500 $OD_{600}$ and most preferred at least 1000 $OD_{600}$. In particular, in a fed batch process according to the present invention cell densities between 50 $OD_{600}$ up to more than 1000 $OD_{600}$ can be obtained.

For illustration, 1 $OD_{600}$ corresponds to about 0.322 g dry mass per liter in average. Consequently, an $OD_{600}$ value of 100 corresponds to 32.2 g dry mass per liter and 500 $OD_{600}$ 161 g dry mass per liter.

Moreover, the host cells according to the present invention allow a high duplicating rate without loss of the vector.

Following expression in the host cell, the expressed product such as a polypeptide of interest can than be recovered from the culture of host cells. In order to obtain a maximum yield of the expressed product the cells are usually harvested at the end of the culture and lysed, such as lysing by lysozyme treatment, sonication or French Press. Thus, the polypeptides are usually first obtained as crude lysate of the host cells. They can then be purified by standard protein purification procedures known in the art which may include differential precipitation, molecular sieve chromatography, ion-exchange chromatography, isoelectric focusing, gel electrophoresis, affinity, and immunoaffinity chromatography. These well known and routinely practiced methods are described in, e.g. Ausubel et al., supra., and Wu et al. (eds.), Academic Press Inc., N.Y.; Immunochemical Methods In Cell And Molecular Biology. For example, for purification of recombinantly produced immunoglobulins, they can be purified with immunoaffinity chromatography by passage though a column containing a resin which has bound thereto target molecules to which the expressed immunoglobulins can specifically bind.

The present invention also relates to methods and means for the intracellular heterologous expression of nucleic acids encoding e.g. polypeptide in a prokaryotic host. In particular the present invention relates to vectors and the use of such vectors for the intracellular expression of a heterologous polypeptide in a prokaryotic host using the vector of the present invention. In intracellular expression the polypeptide is expressed within the cytoplasm and is not transported from the cytoplasm to non-cytoplasmic locations. The polypeptide will be expressed within the cytoplasm in form of inclusion bodies or in soluble form. Procedures for isolating and purifying polypeptides from the cell, in particular from the cell extract, are also well known.

The mannose promoters of the present invention are advantageous in that they can be tightly regulated, induced by a common and non-toxic and therefore industrially useful compound. Further, the mannose promoters of the present invention as well as vectors comprising that mannose promoters are stable within the cells and are not lost even after a plurality of duplications of the cells. Thus, high cell density fermentation with the host cells transformed according to the present invention is possible.

Those skilled in the art will appreciate the invention described herein is susceptible to variations and modifications other than those specifically described. It is to be understood that the invention includes all such variations and modifications without departing from the spirit or essential characteristics thereof. The invention also includes all of the steps, features, compositions and compounds referred to or indicated in this specification, individually or collectively, and any and all combinations or any two or more of said steps or features. The present disclosure is therefore to be considered as in all aspects illustrated and not restrictive, the scope of the invention being indicated by the appended claims, and all changes which come within the meaning and range of equivalency are intended to embraced therein. Various references are cited throughout this specification, each of which is incorporated herein by reference in its entirety.

The foregoing description will be more fully understood with reference to the following examples. Such examples are however exemplary of methods of praciticising the present invention and are not intended to limit the scope of the invention.

I) Isolation and Identification of Promoter Regions of manR Promoter and manP Promoter of Mannose Operon If not stated otherwise the following materials and methods has been used:

Bacterial Strains and Growth Conditions

*E. coli* JM109 (Yanisch-Perron C. et al., Gene 33, 1985, 103-119) and *Bacillus subtilis* 3NA (Michel J. F. et al., J. Appl. Bacteriol. 33, 1970, 220-227) were used as main hosts for cloning and expression. *E. coli* was grown in LB liquid medium (Luria S. E. et al., Virology 12, 1960, 348-390) and LB agar plates supplemented with 100 µg ml$^-$ ampicillin or spectinomycin at 37° C. *B. subtilis* was grown in LB liquid medium and C or S minimal medium at 37° C. (Martin-Verstraete I. et al., J. Mol. Biol. 214, 1990, 657-671). Liquid media and agar plates were supplemented with 100 µg ml$^{-1}$ spectinomycin, 10 µg ml$^{-1}$ kanamycin or 5 µg ml$^{-1}$ erythromycin, respectively. For induction of the mannose promoter, sterile filtered or autoklaved D-mannose was added to a final concentration of 0.2% (w/v).

Materials

All chemicals were obtained from Sigma-Aldrich (Taufkrichen, Germany), Fluka (Buchs, Germany) or Merck (Darmstadt, Germany). Synthetic DNA oligonucleotides were purchased from Eurofins MWG Operon (Ebersberg, Germany). Restriction enzymes and DNA modifying enzymes were purchased from Roche Applied Science (Mannheim, Germany) or New England Biolabs. (Frankfurt am Main, Germany). PCRs were run with High Fidelity-DNA polymerase from Fermentas (ST. Leon-Rot, Germany) on a MiniCycler from Biozym.

Preparation of DNA and Transformation

DNA-isolation from *E. coli* and *B. subtilis* or from agarose gel were carried out with DNA preparation kits of Qiagen (Hilden, Gemrany) or Roche (Mannheim, Germany) as described by the manufacturer. Standard molecular techniques were used throughout the examples.

*E. coli* was transformed with plasmid DNA as described by Chung C. T. et al., Proc. Natl. Acad. Sci. USA 86, 1989, 2172-2175. *B. subtilis* was transformed with plasmid DNA according to the modified "Paris method" (Harwood C. R. Molecular Biological Methods for *Bacillus*, 1990, John Wiley & Sons Ltd., England).

β-Galactosidase Activity Measurement 0.1 ml of the cells to be examined in 0.9 ml Z-buffer were treated with 10 µl toluene for 30 min at 37° C. The β-galactosidase activity was determined with o-nitrophenyl-β-galactopyranoside at 22° C. according to Miller's method (Miller J. H., 1972, experiments in molecular genetics, Cold Spring Harbor, N.Y.).

Oligonucleotides Used between manR and manP was amplified from the obtained DNA by PCR using primer s4693/s4694.

The obtained DNA fragment of about 2.3 kb was used for a primer extension experiment for determining the transcription initiation sites of manR promoter and manP promoter.

For isolation of mRNA for primer extension a shuttle factor was constructed from the *E. coli* vector pIC20HE (Altenbuchner et al., 1992, Methods Enzymol. 216, 457-466) and the *B. subtilis* vector pUB110 (MacKenzie et al., 1986, Plasmid 15, 93-103). The vector contained the lys gene as reporter gene, which codes for the mature form of lysostaphin from *Staphylococcus simulans* (Recsai et al., 1987, Proc. Natl. Acad. Sci. USA 84, 1127-1131). Into this high copy pUB110 derivative the 2.3 kb DNA fragment was cloned upstream to

TABLE 1

| Oligo-nucleotide | Sequence | Purpose |
|---|---|---|
| s4693 | 5'-AAA AAA ACG CGT GTT AAA ACT GAA TTT CTG CTG AAT ATA CA-3' | PCR amplification of manR from *B. subtilis* |
| s4694 | 5'-AAA AAA TCT AGA AAG TGT GAA TAA TAA GAT CTT G-3' | PCR amplification of manR from *B. subtilis* |
| s4802 | 5'-AAA AAA ACT AGT GTT AAA ACA GGG AAA AAT GCC TTT ATT AC-3' | Forward primer for amplification of $P_{manP\Delta 3}$ |
| s4833 | 5'-AAA AAA GTT AAA CCC CTG GCG AAT GGC GAT-3' | Amplification of spc from plasmid pDG1730 |
| s4835 | 5'-AAA AAA GAA TTC ATT AGA ATG AAT ATT TCC CAA AT-3' | Amplification of spc from plasmid pDG1730 |
| s4956 | 5'-AAT TGC GTC GAG ACC CCT GTG GGT CTC GTT TTT TGG ATC CGG CGC CCA CGT GGC TAG CC-3' | Insertion of tufA terminator |
| s4957 | 5'-TTA AGG CTA GCC ACG TGG GCG CCG GAT CCA AAA AAC GAG ACC CAC AGG GGT CTC GAC GC-3' | Insertion of tufA terminator |
| s5006 | 5'-Cy5-TAG CCT TTT TTA TAG TTG TTC AGC CAC TGT-3' | Labeled primer for primer extension |
| s5007 | 5'-Cy5-ATC CAC GCC ATA ATG CAT GCC GCC ATT AAT-3' | Labeled primer for primer extension |
| s5097 | 5'-Cy5-CACTGTACCCTATCTGCGAAA-3' | Labeled primer for primer extension |
| s5098 | 5'-Cy5-ATTGAGATAATCCTCGATCACTT-3' | Labeled primer for primer extension |
| s5203 | 5'-GATATCCTGCACCATCGTC-3' | Backward primer for amplification of PmanP for promoter study |
| s5208 | 5'-GGTACCATTTCTTGCTGAATA-3' | Amplification of $P_{manR}$-region from pSUN279.2 |
| s5209 | 5'-CTTAAGCCTGTCAGTATCTACTTGAG-3' | Amplification of $P_{manR}$-region from pSUN279.2 |
| s5262 | 5'-AAAAAAGCTAGCGTTTAAACAAAAAGCGATT TTAATGAGCTG-3' | Forward primer for amplification of $P_{manP\Delta 4}$ |

Experiment 1

Isolation of DNA fragment carrying the promoter regions of the mannose operon and determination of transcription initiation sites of manR promoter and manP promoter.

Chromosomal DNA of *Bacillus subtilis* 168 was isolated by using DNeasy Blood & Tissue Kit of Qiagen (Hilden, Germany).

A DNA fragment of about 2.3 kb with the complete manR with the putative manR promoter and the intergenic region the lysostaphin gene. The resulting plasmid was named pSUN178.4 and introduced into *Bacillus subtilis* 3NA.

*Bacillus subtilis* 3NA with plasmid pSUN178.4 was grown in LB medium with kanamycin. In the exponential growth phase the culture was induced with 0.2% mannose. After 1 hour growth at 37° C. the induced and non-induced cells were harvested. Total RNA was isolated with the Qiagen-RNeasy Mini Kit.

With Cy5 at the 5'-end labeled primers s5006, s5007, s5097 and s5098 were used.

Primer s5006 and s5007 hybridized respectively from +21 to +50 and from +76 to +105 with respect to the start codon of lysostaphin gene. Primer s5097 and s5098 hybridized respectively from +81 to +101 and from +131 to +153 with respect to the start codon of manR. The same primers were used for the sequencing reaction of plasmid DNA of pSUN178.4, which served as size standard. The AMV-Reverse Transcriptase and T7-DNA polymerase from Roche were used, respectively, for the reverse transcription and DNA sequencing. The products of reverse transcription and sequencing were analyzed on a denaturating polyacrylamide sequencing gel (GE healthcare). All other reagents used were provided by Amersham Pharmacia Biotech AutoRead Sequencing kit.

The transcription initiation site of manP-promotor was determined by using primer s5006. DNA sequence reactions of the plasmid pSUN 178.4 with the same primer were prepared and run on the same denaturing gel for comparison. FIG. 1 shows the DNA sequence around the manP promoter with the transcription initiation site at A (adinine nucleotide) being highlighted. The deduced −10 and −35 boxes are in italics, the end of the manR gene and start of the lys gene are marked by arrows, restriction sites for Bgl-II, XbaI, AflII and NdeI are underlined.

The transcription initiation site of manR promoter was determined with RNA isolation and DNA sequencing being carried out as described above with respect to manP promoter except that primer s5098 was used which binds in the manR gene. In FIGS. 2 and 3 the DNA sequence of the manR promoter region is shown with the transcription initiation site at G (guanine nucleotide) being highlighted, the deduced −10 and −35 boxes in italics, and the start of the lys gene and manR gene, respectively, being indicated by an arrow. The restriction sites and a putative cre sequence are underlined.

The transcription from the manR promoter and in particular from the manP promoter was strongly increased when the cells were induced by mannose as was seen by the much stronger signals in the primer extension experiment.

The primers used are shown in table 1 above.

Experiment 2

The primer extension experiment according to Experiment 1 located the transcription initiation site of the manP promoter near the 3'-end of the intergenic region between manR and the beginning of manP. For determining the manP promoter region more precisely the 2.3 kb DNA fragment was shortened step-by-step by PCR-amplification, the obtained sequence fragments of different lengths cloned back to the same basic expression vector and expression was studied.

a) Construction of Basic Expression Vector

An expression vector with promoterless lacZ as reporter gene was constructed. The expression vector was designed as a shuttle vector capable of replicating both in B. subtilis and in E. coli and named pSUN272.1.

The reporter gene lacZ was cut with NdeI and XmaI from pLA2 (Haldimann A. et al, 2001, J. Bacteriol. 183, 6384-6393) and ligated into pJOE5531.1, a derivate of the rhamnose inducible expression vector pWA21 (Wegerer et al., 2008, BMC. Biotechnol. 8, 2) which contained the B. subtilis tufA transcription terminator at the XmaI site. Into this plasmid a pair of oligonucleotides s495614957 was inserted between the AflII/MunI restriction sites in order to add the same tufA transcription terminator upstream of lacZ. So the "reading through" from plasmid promoters into lacZ as well as "reading through" out of lacZ into the flanking plasmid sequences was avoided by the terminators. A spectinomycin resistance gene spc for both E. coli and B. subtilis was amplified from plasmid pDG1730 (Geurout-Fleury et al., 1996, Gene 180, 57-61) with oligonucleotides s4833/4835 and inserted into the plasmid obtained above. In addition, the E. coli vector part was shortened by deleting a BspHI/HindIII fragment. Subsequently, an EcoRI/SphI fragment with the replication region of B. subtilis pMTLBS72 (Lagodich et al., 2005, Mol. Biol. (Mosk) 39, 345-348) was ligated into the plasmid.

The 2.3 kb DNA fragment obtained in Experiment 1 was inserted into pSUN272.1 in front of lacZ by digesting with AflII and NheI and ligation, thereby obtaining expression vector pSUN279.2 with the plasmid map as shown in FIG. 4. The primers used are shown in table 1 above.

b) Determination of Expression Efficiency of Vector pSUN279.2

Figure 5:
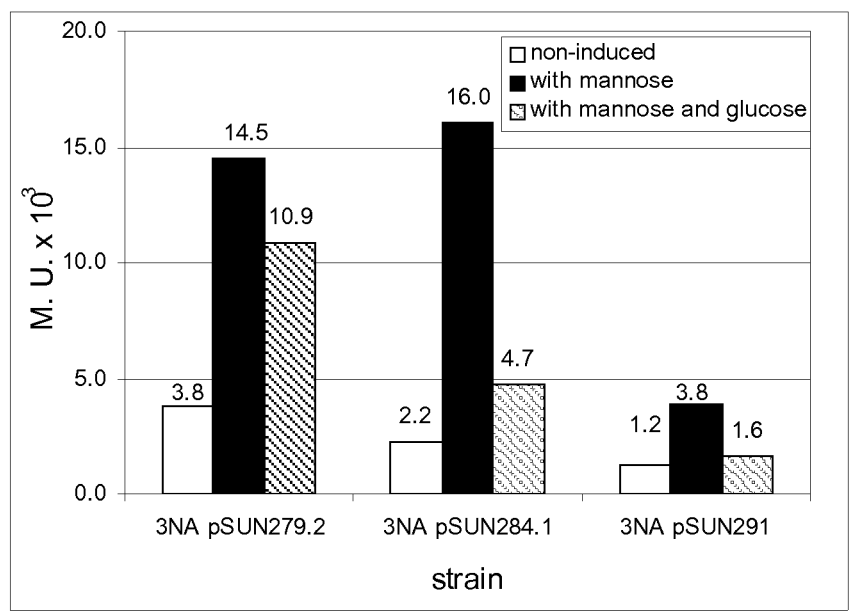
FIG. 5 the β-galactosidase activities of *B. subtilis* 3NA containing the plasmids pSUN 279.2, pSUN 284.1 and pSUN 291, respectively, according to the present invention.
Figure 7:
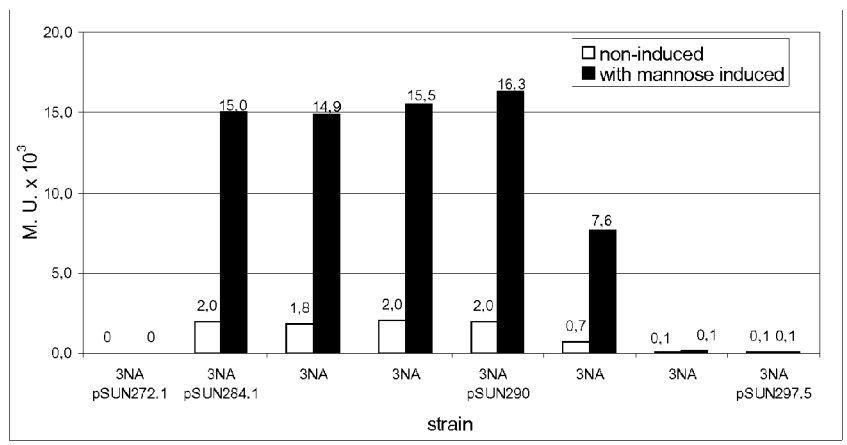
FIG. 7 the β-galactosidase activities of *B. subtilis* 3NA containing the plasmid pSUN 279.2 as well as of further plasmids containing fragments of different lengths of the nucleic acid sequence shown in FIG. 6.

The plasmids pSUN279.2 and pSUN272.1 obtained in a) above were brought into B. subtilis 3NA. The latter served as background control. The B. subtilis 3NA strains carrying one or the other plasmid were grown in LB medium with spectinomycin and in the exponential growth phase either 0.2% mannose, 0.2% mannose plus 0.2% glucose or no sugar (uninduced control) were added to the cultures for induction. After one hour induction the β-galactosidase activity of the cells was determined through Miller's assay. The results are shown in FIGS. 5 and 7.

The non-induced culture of B. subtilis containing pSUN279.2 showed already a quite high basal level of β-galactosidase activity. The presence of mannose resulted in a further 4-fold increase of β-galactosidase activity whereas the activity with mannose and glucose was reduced but was still quite above the basal level. The results clearly indicate that the promoter activity seen in pSUN279.2 could originate from the region between manR and manP, from the region upstream of manR or from both.

Therefore, the upstream region of manR as well as most part of manR were both deleted from pSUN279.2 by cutting the 2.3 kb DNA fragment of pSUN279.2 as shown in FIG. 4 between SfoI and NruI to give plasmid pSUN284.1. The resulting nucleic acid sequence of pSUN284.1 is shown in FIG. 6.

B. subtilis 3NA was transformed with this plasmid pSUN284.1 and the expression efficiency determined as set out above. The result is shown in FIG. 5. As can be seen from FIG. 5 this manR deleted vector pSUN284.1 in B. subtilis 3NA showed only about half of the basal level of β-galactosidase activity compared to pSUN279.2 in B. subtilis 3NA, an even stronger increase by mannose induction and again a stronger reduction in the presence of glucose. These results prove that the manP promoter is located between manR and manP and show that the chromosomal copy of manR is sufficient for regulating all manP promoter copies on the low copy plasmids.

c) Localization of manP Promoter Region

Figure 6:
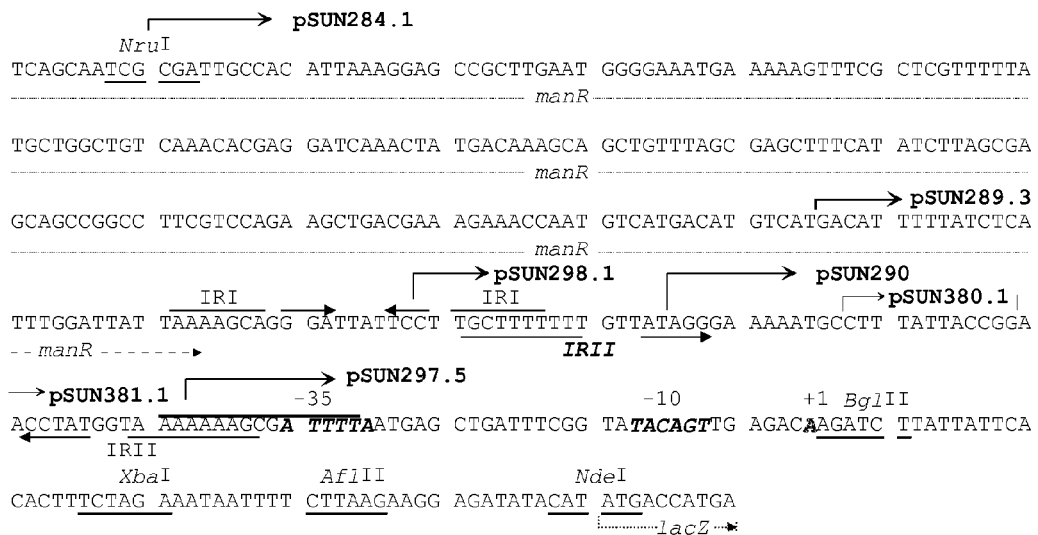
FIG. 6 the nucleic acid sequence obtained from *B. subtilis* comprising the promoter region of manP promoter from *B. subtilis* including the C-terminal end of manR, the intergenic region between manR and manP, here replaced by reporter gene lacZ, with the transcription start site, the −35 and −10 boxes being in bold type, the end of manR and start of lacZ being indicated by an arrow and the restriction sites being underlined; said sequence comprising SEQ ID No. 2.

For localizing the promoter region of manP in addition to the shortened DNA fragment of pSUN284.1 further shortened sequence fragments were prepared from the 2.3 kb DNA fragment by cutting at different positions upstream to the transcription initiation site of manP promoter at restriction sites and by restriction enzymes as shown in FIG. 6.

Deletion down to by −81 and by −80 upstream to the transcription initiation site of manP resulted in a second deletion sequence comprising SEQ ID NO. 1.

A further deletion was carried out down to by −41 and by −40 upstream to the transcription initiation site of manP (third deletion sequence).

Plasmids comprising the second deletion sequence, pSUN290, and the third deletion sequence, pSUN297.5 were constructed in a similar way as plasmid pSUN284.1 in 2b) above, by inserting the PCR products amplified with primers s4802/s5203 and s5262/s5203, respectively, into pSUN272.1 via restriction enzymes EcoRV and NheI.

The plasmids were inserted into *B. subtilis* 3NA and cultured as set out above in b) After 1 hour induction the β-galactosidase activity of the cells was determined as set out in b) above. The results are shown in FIG. 7.

As shown in FIG. 7 none of the strains with pSUN290 and pSUN284.1 showed a significant difference concerning induction of lacZ by mannose. However, in *B. subtilis* 3NA comprising pSUN297.5 with the third deletion sequence, induction by mannose was completely abolished and the basal expression level was nearly 0. From these results follows that the ManR binding site of the manP mannose promoter region is located between by −80 and −35 with respect to the transcription initiation site of manP.

Experiment 3

Determination of manR Promoter a) Identification of Cre Sequence

Since most CCR is mediated through catabolite control protein A (CcpA) a search for the respective binding sites (cre sequence) was carried out in the whole mannose operon using the DNA alignment function in the Clone Manager program. For the alignment the cre consensus sequence 5'-WWTG-NAARCGNWWWCAWW-3' was used.

Only in the promoter region of manR one putative cre sequence was found as shown in FIGS. 2 and 3 which is located downstream to the −10 box.

SEQ ID NO. 3 of the present invention encompasses the region starting from by −122 down to the start codon of lacZ, SEQ ID NO. 4 encompasses the region starting from by −122 to bp+7 (inclusive) and SEQ ID NO. 5 of the present invention encompasses the region starting from by −122 to bp−1 (inclusive) of the sequence shown in FIG. 3.

b) Evaluation of Expression Efficiency of manR Promoter

For evaluating the expression efficiency of the manR promoter an expression vector like pSUN284.1 was constructed as set out above and named pSUN291. To this, a DNA fragment including the putative manR-promoter and about 600 bp upstream of manR was amplified with primer s5208/s5209 and linearized plasmid DNA pSUN279.2 as template and inserted in front of lacZ in plasmid pSUN272.1, by digesting with KpnI and AflII and ligation. The DNA-sequence is shown in FIG. 3. Plasmid pSUN291 was introduced into *B. subtilis* 3NA and the β-galactosidase activity was measured as set out above in experiments 2 b).

The result is shown in FIG. 5. Here, the basal expression was already relatively high and was further increased about 3-fold by addition of 0.2% mannose.

Addition of glucose led to repression of β-galactosidase activity to nearly the basal expression level. The result indicated that the manR promoter is not just a weak constitutive promoter but subject to mannose and CCR regulation.

c) Localization of manR Promoter Region

As in experiment 2c) for further localization of the promoter region of manR DNA-sequence DNA-fragments of different lengths were prepared from the DNA-sequence as contained in pSUN291 by cutting at different positions upstream to the transcription initiation site of manR promoter at restriction sites and by restriction enzymes as shown in FIG. 3. A first deletion sequence was obtained by cutting the sequence shown in FIG. 3 down to by −100 and by −99 upstream of the transcription initiation site G, a second deletion sequence was obtained by cutting down to by −83 and by −82 upstream of the transcription inition site G.

Analogous to experiment 2c) the obtained first and second deletion sequences were introduced into pSUN272.1 and the resulting plasmids named pSUN384.1 and pSUN385.2, respectively.

Each plasmid was inserted into *B. subtilis* 3NA and cultured as set out in experiment 2b. After one hour induction the β-galactosidase activity of the cells was determined as set out in experiment 2b. The results are shown in FIG. 8. There is no significant difference concerning induction of lacZ by mannose of pSUN384.1 compared to pSUN291. However, in *B. subtilis* 3NA comprising pSUN385.2 with the second deletion sequence, induction by mannose was completely abolished and the basal expression level was nearly 0. From this results follows that the ManR binding site of the manR promoter region is located between bp−99 and bp−35 with respect to the transcription initiation site of manR.

II) Use of the Promoter Regions of Mannose Operon in High Cell Density Fermentation Experiment 4

Transformation

A model host carrying the promoter region of the present invention was tested for its growth and expression capability. Using the nucleic acid sequence according to the manP promoter region as introduced in plasmid pSUN284.1 as shown in FIG. 6 and as used in experiment 2c, plasmid pMW168.1 was constructed as set out below and introduced into *B. subtilis* 3NA as host by transformation.

a) Construction of Plasmid pMW168.1

A shuttle vector replicable in both *E. coli* and *B. subtilis* was designed as set out in Experiment 2a) with the exception that eGFP was used as reporter gene instead of lacZ. Also the transcription initiation region of manP was replaced by that of the gene gsiB (Stress protein; Jürgen et al., supra).

Further, the start codon of eGFP and 6 codons following the start codon were replaced.

The schematical structure of the obtained promoter- and transcription initiation region is shown in FIG. 17.

Shown is the arrangement of the genes (arrows) and the regions (boxes) with the relevant restriction sites.

Figure 18:
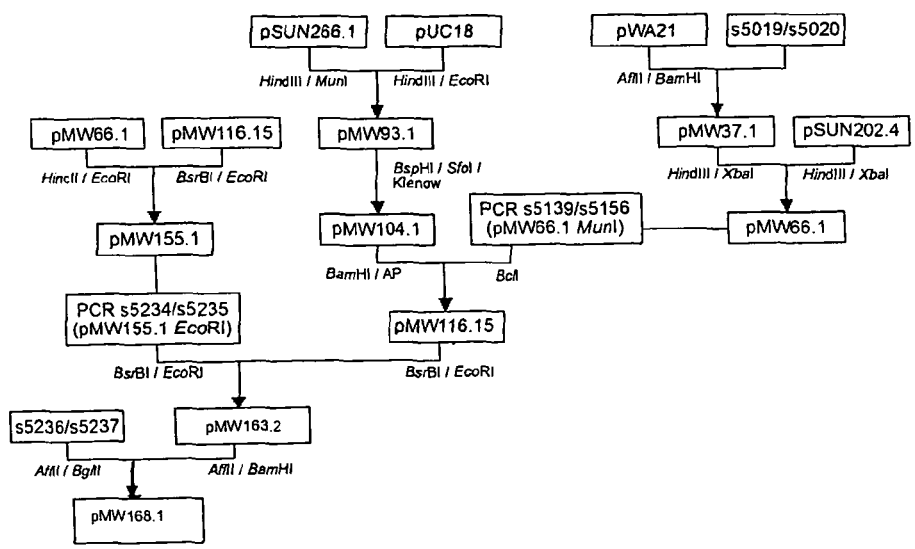
FIG. 18 flow chart of the construction of plasmid pMW168.1.

Generally, plasmid pMW168.1 was obtained as shown in the flow chart in accordance to FIG. 18.

In the flow chart the names of the vector-DNAs, the insert-DNAs and the complementary oligonucleotides used were as indicated in the boxes, with respect to the products of PCR the primers and the template-DNA were as within the brackets, the restriction enzymes used were indicated at the respective sites.

The cloning steps were carried out with *E. coli* JM109.

The plasmids used were pUC 18 a positive selection and cloning vector for PCR products with amp-resistance (Yanosch-Perron et al., supra); pWA21 an expression and cloning vector for *E. coli* with amp-resistance (Wegerer et al., 2008, BMC Biotechnol. 8,2); pSUN202.4 a pUB 110 derivate with manP promoter region and amp and kan resistance, being a shuttle vector for *E. coli* and *B. subtilis*; and pSUN266.1 a pUC18 derivate with integration site between ter-sequences and spc and amp resistance.

The sequence of the primers used was as follows:

| Name | sequence 5' → 3' | description |
|---|---|---|
| s5019 | ttaagCTCTTAAGGAGGATTTTAGAATGGCTAAAGAAAAATTCg | tufA TI-Region |
| s5020 | ttaagGAATTTTTCTTTAGCCATTCTAAAATCCTCCTTAAGAGg | tufA TI-Region (compl.) |
| s5139 | aaaaaatgatcaTTACTTGTACAGCTCGTC | f-Primer PmanP-eGFP |
| s5156 | aaaaaatgatcaccggtCGATTGCCACATTAAAGG | r-Primer PmanP-eGFP |
| s5234 | aaaaaaccgCTCGTCTTCCTAAGCATCCT | f-Primer rep (pUB110) |
| s5235 | aaaaaagaatTCGAGATCAGGGAATGAGTTT | r-Primer rep (pUB110) |
| s5236 | ttaagAATTAAAGGAGGAATTCAAAATGGCAGACAATAACAAAg | gsiB TI-Region |
| s5237 | gatccTTTGTTATTGTCTGCCATTTTGAATTCCTCCTTTAATTc | gsiB TI-Region (compl.) |

Replacement of the transcription initiation region inclusive the start codon and the codons following the start codon were carried out using complementary oligonucleotides and via the single restriction sites BglII, AflII and BamHI. The construction of the vector started with the replacement of the transcription initiation region of the T7 gene 10 of vector pWA21 (Wegerer et al., supra) by the translation initiation region of tufA from B. subtilis via complementary oligonucleotides s5019 and s5020, respectively. In further cloning steps this transcription initiation region was replaced by that of gsiB. The final plasmid pMW168.1 contained the rep gene inclusive ori+ from pUB110.

The plasmid map of pMW168.1 is shown in FIG. 9.

b) Determination of Structural Stability and Segregation

B. subtilis 3NA was transformed with vector pMW168.1 and the structural stability as well as stable propagation of the vector on cell division (segregation) was determined.

B. subtilis 3NA transformed with pMW168.1 was precultured in $LB_{Spc}$-medium and then transferred into $LB_0$-medium without selection pressure.

Incubation was carried out at 37° C. At the end of the exponential growth phase each culture was inoculated into fresh $LB_0$-medium. This procedure was repeated until 100 generations were obtained calculated based on the measured OD-values obtained during transfer into fresh medium in accordance to the modified method of Harwood et al., 1990, Molecular Biological Methods for Bacillus, John Wiley & Sons Ltd. The result is shown in FIG. 10.

After about 15 generations more than 99.9% of the cells and even after 20 generations about 90% of the cells still carried the vector. Only from about the 25$^{th}$ generation more and more cells lost the vector.

For determining structural stability of the plasmid, from 20 colonies the plasmid was isolated after 15 generations. About 0.5 µg of each isolated plasmid was compared with pMW168.1 isolated from E. coli as control by agarose gel electrophoresis. No differences in the runs of the plasmids and the control were observed indicating that no structural variation had occurred.

These results show that plasmid pMW168.1 not only has a high structural stability but also stable segregation as desired in fermentation.

Experiment 5

Fermentation

Six fermentation runs were conducted with B. subtilis 3NA transformed with plasmid pMW168.1 comprising the reporter gene eGFP with different induction regimes and monitored online by observing the fluorescence signal of eGFP. As fermentation medium the known medium for high cell density fermentation of E. coli as disclosed in Wilms et al., 2001, Biotechnol. Bioeng. 73, 95-103, and as shown in the following was used.

Materials and Methods

In general, also for the fermentation experiments standard molecular techniques were used if not stated otherwise.

Optical Density

For determining the optical density (OD) the spectrophotometer Ultrospec 1100pro of Amersham Bioscience Company was used at 600 nm in accordance to the protocol of the manufacturer.

Determination of the Dry Biomass Concentration

For the determination of the dry biomass concentration $c_x$ moisture meter MB 835 Halogen of Ohaus Company was used.

Spectophotometrical Measurement of Flurescence

Expression and flurescence, respectively, of eGFP was analyzed by the Multifunction reader GENios of TECAN Company using the reader software X Fluor 4 (version V4.11) with the following measuring parameters:

| Measuring parameter | value |
|---|---|
| Excitation filter | 485 nm |
| Emission filter | 535 nm |
| Gain (manual) | 60 |
| Integration time | 20 µs |
| Number of flashes | 3 |
| Read mode | Top |

Online Fluorescence Measurement in Fermentor

During the fermentation the expression of eGFP was monitored online using the fluorescence probe (Micropack HPX-2000, High Power Xenon Lightsource of Ocean Optics, Inc.;

S2000 fiber optic spectrometer). The measuring parameters were as follows: excitation filter 485 nm, emission filter 535 nm, filter 0.6). For recording and storage Ocean Optics SpectraSuite Software was used. Fluorescence is indicated as relative flurescence unit (RFU). Shortly before obtaining 4.000 RFU the integration time of 50 ms was changed to 25 ms and then to 10 ms. In these cases the measuring values were multiplicated by factor 2 and 5, respectively.

Cultivation of Pre-Cultures

A single colony was placed onto a LB agar plate and cultured overnight in 5 ml Spizizens minimal medium (SMM) including 0.02% (w/v) Casamino acids (CA) and antibiotic. 1 ml of the overnight culture was added to 20 ml SMM with 0.02% (w/v) CA and antibiotic and incubated 5-6 h at 37° C. in a 250 ml Erlenmeyer flask (pre-culture 1). 10 ml of pre-culture 1 were added to 200 ml batch medium including 5 g/l glucose and incubated up to 8 h at 37° C. in a 1 l Erlenmeyer flask (pre-culture 2). For inoculation of the fermentors pre-culture 2 with $OD_{600}$ between 1.2 and 2.2 was used.

Fermentation

In general, fermentation was carried out in accordance to the principles of Wilms et al., 2001, Biotechnol. Bioeng. 73, 95-103. As soon as glucose, the carbon source, was completely consumed the batch mode was switched to the fed-batch mode.

By adding the feed solutions exponentially in the fed-batch phase, a constant growth rate of $\mu=0.10\ h^{-1}$ can be obtained and at the same time catabolite repression by glucose is avoided, because of the immediate consumption of glucose by the cells.

Protein Analysis

The crude protein extracts of the harvested cells were analyzed by SDS-polyacrylamide gel electrophoresis with a polyacryl amide gel consisting of 3% stacking gel and 12% separation gel with the following composition:

| Component | Stacking gel (3%) | Separating gel (12%) |
| --- | --- | --- |
| deionized $H_2O$ | 3.00 ml | 6.70 ml |
| TRIS 0.5M pH 6.8 | 1.25 ml | — |
| TRIS 1.5M pH 8.8 | — | 5.00 ml |
| SDS 10% (w/v) | 0.05 ml | 0.20 ml |
| acryl amide 30% (w/v) | 0.67 ml | 8.00 ml |
| APS 10% (w/v) | 0.05 ml | 0.10 ml |
| TEMED | 0.005 ml | 0.01 ml |

A Twin Mini gel chamber of Biometra company was used.

For denaturation 12 µl crude extract of protein mixture was mixed with 3 µl 5×SDS-application buffer and incubated in Thermomixer 5438 of Eppendorf company for 5 minutes at 95° C. After cooling to room temperature the samples were separated by centrifugation and completely put onto the gel. During separation in the stacking gel the current was 10 mA and was increased to 20 mA after the frontiere of Bromphenol reached the stacking gel. 1×SDS-running puffer and the lengths standard ROTI®-Mark of Roth company were used for separation. The electrophoresis was finished as soon as the Bromphenol frontiere run completely out of the gel. For detection of the distinct protein bands the gel was incubated with Coomassie staining solution for 30 minutes at room temperature and was subsequently treated with de-staining solution for further 30 minutes at room temperature. For removing the remaining blueish background out of the gel the gel was incubated for several hours in 7.5% acetic acid.

The composition of the buffer solutions and of the staining as well as de-staining solutions were as follows:

| Buffer/solution | Components | Concentration |
| --- | --- | --- |
| Coomassie staining solution | Coomassie R250 | 2.0 g |
| | Coomassie G250 | 0.5 g |
| | EtOH | 425 ml |
| | MeOH | 50 ml |
| | glacial acetic acid | 100 ml |
| | deionized $H_2O$ | ad 1.0 l |
| de-staining solution | EtOH | 450 ml |
| | glacial acetic acid | 100 ml |
| | deionized $H_2O$ | 450 ml |
| 5x application buffer | TRIS/HCl (2M, pH 6.8) | 6.25 ml |
| | EDTA | 0.146 g |
| | SDS (40% (w/v)) | 6.25 ml |
| | β-mercaptoethanol (pure) | 2.50 ml |
| | glycerine (86% (v/v)) | 29.00 ml |
| | Bromphenol blue | 0.05 g |
| | deionized $H_2O$ | ad 50 ml |
| 10x running buffer | TRIS | 30 g |
| | glycine | 144 g |
| | SDS (20% (w/v)) | 50 ml |
| | deionized $H_2O$ | ad 1.0 l | with TRIS: Tris(hydroxymethyl)aminomethane
SDS: Sodium dodecylsulfate
APS: Ammonium persulfate
TEMED: N,N,N',N'-Tetramethylethylenediamine,
EDTA: Ethylenediaminetetraacetic acid.

Induction of Gene Expression

For induction of the gene expression different modes of addition of the inducer solution (induction regime) were evaluated:

1. Addition in a single portion at a given point of time (impact induction)
2. Impact induction combined with a further induction over a time interval wherein
   the further addition was at a constant rate with step-wise increasing amounts or
   the further addition was in an exponentially increasing rate,
3. Start of addition of inducer solution upon reaching a given cell density.

TABLE 2

| Media used | | |
| --- | --- | --- |
| medium | component | concentratrion |
| $LB_0$-Medium (pH 7.2) | Trypton | 10.0 g |
| | yeast extract | 5.0 g |
| | NaCl | 5.0 g |
| | $H_2O$, de-ionized | ad 1.0 l |
| Spizizens Minimalmedium (SMM) | $(NH_4)_2SO_4$ | 2.0 g |
| | $KH_2PO_4$ | 6.0 g |
| | $K_2HPO_4$ | 14.0 g |
| | $Na_3$Citrate | 1.0 g |
| | $MgSO_4$ | 0.2 g |
| | D-Glucose* | 5.0 g |
| | $H_2O$, de-ionized | ad 1.0 l |
| Batch-Medium für B. subtilis fermentations | $(NH_4)_2$H-Citrat | 1.00 g/l |
| | $Na_2SO_4$ | 2.68 g/l |
| | $(NH_4)_2SO_4$ | 0.50 g/l |
| | $NH_4Cl$ | 0.50 g/l |
| | $K_2HPO_4$ | 14.60 g/l |
| | $NaH_2PO_4 \times H_2O$ | 4.00 g/l |
| | D-Glucose* | 25.00 g/l |
| | $MgSO_4$(1m)* | 2.00 ml/l |
| | TES* (as below) | 3.00 ml/l |

*to be autoclaved separately

| Trace element solution (TES) | $CaCl_2 \times 2H_2O$ | 0.50 g/l |
|---|---|---|
| | $FeCl_3 \times 6H_2O$ | 16.70 g/l |
| | $Na_2$-EDTA | 20.10 g/l |
| | $ZnSO_4 \times 7H_2O$ | 0.18 g/l |
| | $MnSO_4 \times H_2O$ | 0.10 g/l |
| | $CuSO_4 \times 5H_2O$ | 0.16 g/l |
| | $CoCl_2 \times 6H_2O$ | 0.18 g/l |

The pH was adjusted with 2 M NaOH and 1 M HCl solution, respectively. For agar plates 15 g/l Euroagar of BD company, were additionally added.

All media were autoclaved at 121° C. for about 30 min.

Fermentation run 1: Impact Induction

Fermentation run 1 was carried out in a 30 l reactor (D598 and D596 of Bioengineering). The batch volume was 8 l. Depending on $OD_{600}$ 200-400 ml pre-culture 2 were inoculated for adjusting the start $OD_{600}$ to 0.1. During the batch phase the temperature was 30° C. overnight and after 12 h increased to 37° C. By addition of 24% (v/v) $NH_4OH$ the pH was adjusted to about 7.0 during the whole fermentation. The aeration rate could be adjusted up to 30 l/min. At the beginning of the batch phase the aeration rate was 10 l/min.

The composition of the feed media I and II were shown as below in table 3.

TABLE 3 composition of feed media I and II

| Feed medium I | | Feed medium II | |
|---|---|---|---|
| Component | Concentration | Component | Concentration |
| glucose*$H_2O$ | 654.76 g/l | $(NH_4)_2HPO_4$ | 396.00 g/l |
| $MgSO_4 \ast 7H_2O$ | 25.50 g/l | Adjusted to pH 7.0 | |
| *TES | 120.00 ml/l | Overall volume | 1.0 l |
| $H_2O$ de-ionized | ad 4.2 l | $H_2O$, de-ionized | ad 1.0 l |

*trace element solution
pH 7.0

Media I and II were added in proportion to their overall volumes, i.e. 4.2:1.0 (corresponding to 80.8% medium 1 and 19.2% medium II of the overall feed F).

For induction at the beginning of the fed-batch phase 0.2% (w/v) D-mannose solution was added in one portion.

The dry biomass concentration and the monitored fluorescence signal are shown in FIGS. 11a and 11b, respectively. In the figure the concentration of the dry biomass $c_x$ is plotted logarithmically over the duration of the culture. Batch and fed-batch phase are separated by the perpendicular line. The monitored fluorescence signal at 535 nm emission wavelength is plotted over the culture period. Arrows indicate the point of induction.

From FIG. 11a results that a maximal dry biomass (DM) concentration of 82.75 g DM/l was obtained corresponding to about 970 g DM based on the reaction volume of 11.7 l. In total 71.5 g of inducer D-mannose was consumed with 16 g in the first addition. The specific growth rate μ was 0.10 $h^{-1}$ during the whole fed-batch phase.

As shown in FIG. 11b the fluorescence signal strongly increased after the first addition of D-mannose up to a maximum of about 2,200 RFU within the first five hours of the fed-batch phase. Then, the signal continuously decreased. It is assumed that this decrease in expression rate is due to the consumption of the inducer and/or to a shielding effect by the increasing cell mass. An addition of further 0.5% (w/v) mannose solution after 37 hours resulted in a new increase of the fluorescence signal up to a value of 2,100 RFU.

Fermentation Run 2: Combined Induction with Constant Rate

The same procedure as in a run 1 was repeated except that the mode of addition of inducer was changed. As in run 1 0.2% (w/v) D-mannose solution was added in a single portion at the starting point of the fed-batch phase. The addition of the second portion of inducer was started as soon as the RFU at the turning point of the curve of the flurescence signal of run 1 was reached, which was 1,500.

During the second addition step 20% (w/v) mannose solution was added in a constant rate with stepwise increasing amounts with an average rate of 0.39 g/min until all of the second portion had been added.

The results are shown in FIGS. 12a and 12b showing the dry biomass concentration and the curve of the fluorescence signal, with the detonation being the same as in FIGS. 11a and 11b. In FIG. 12b the points of addition of the first portion and start and end of addition of the second portion are indicated by arrows.

As results from FIG. 12a the maximal concentration of dry biomass was 67.6 gDM/l corresponding to about 804 g DM based on a reaction volume of 11.9 l. In total (first and second addition) 70 g D-mannose were added. The yield of biomass was decreased by 17% compared to run 1. This correlates with a lower specific growth rate μ=0.09 $h^{-1}$ during the fed-batch-phase, whereas the specific growth rate during the batch-phase was 0.43 $h^{-1}$.

As results from FIG. 12b the maximum of the fluorescence signal was reached at about 4,900 RFU after 25 hours and continuously decreased to about 2500 RFU. Compared to run 1 in run 2 the expression rate could be enhanced by 120% with a slight decrease in biomass concentration.

Fermentation Runs 3 and 4: Combined Induction with Exponential Rate

A 3.7 l small laboratory fermentor (Kleinlaborfermenter of Bioengineering Company) was used in runs 3 and 4. The batch volume (batch medium plus inoculum) was 1.5 l in total. Depending on $OD_{600}$ 100-200 ml of pre-culture 2 were inoculated for adjusting the start $OD_{600}$ to about 0.1. The temperature in both the batch and the fed-batch phase was 37° C. During fermentation the pH was adjusted to 7.0 by 24% (v/v) $NH_4OH$. The aeration rate was constantly 2 l/min during the fermentation. The oxygen input was adjusted by the rotation speed of the stirrer. The fermentation pressure was 1.3 bar at the beginning and was then increased to 1.5 bar to enhance the oxygen input on demand. After complete consumption of the carbon source glucose the batch operation was switched to the fed-batch operation.

Unlike run 2 in runs 3 and 4 the inducer solution was fed in an exponentially increasing rate. Further, glucose containing medium I was co-feeded with the inducer containing medium II. The composition of the feed media I and II were as shown below in table 4:

TABLE 4 composition of feed media I and II

| Feed medium I | | Feed medium II | |
|---|---|---|---|
| Component | Concentration | Component | Concentration |
| D-glucose | 200 g/l | D-mannose | 200 g/l |
| TES | 40 ml/l | TES | 40 ml/l |
| $MgSO_4$ | 3.85 g/l | $MgSO_4$ | 3.85 g/l |
| $(NH_4)HPO_4$ | 63.36 g/l | $(NH)_4HPO4$ | 63.36 g/l |
| $H_2O$ de-ionized | ad 1 .0 l | $H_2O$, de-inonized | ad 0.25 l (run 3) |
| | | | ad 1 l (run 4) |

All components of media I and II were autoclaved separately pH-value was adjusted to 3.3 with 85% (v/v) $H_3PO_4$ in both media because of the solubility of the components.

The total feed F at time t was calculated by the following formula:

$$F(t) = \left(\frac{\mu_{set}}{Y_{X/S}} + m\right) \cdot \frac{C_{x0}V_0}{C_{s0}} \cdot e_{set}^{\mu \cdot t}$$

with
- m=maintainance coefficient. (0.04 g g$^{-1}$H$^{-1}$)
- $Y_{x/s}$=specific yield coefficient of biomass related to substrate (0.5 for glucose)
- $C_{x0}$=biomass concentration at start of fed-batch phase
- $V_0$=reactor volume at start of fed-batch phase (=batch volume)
- $C_{s0}$=glucose concentration in feed solution For the calculation it was assumed that D-mannose was consumed by *B. subtilis* with a comparable yield coefficient $Y_{X/s}$ glucose.

In KLF media I and II could be separately supplied and the proportional ratio could be varied.

a) Fermentation Run 3

The biomass concentration and the monitored fluorescence signal are shown in FIGS. 13a and 13b, with the denotation of the figures being the same as in run 1.

At the beginning of the fed-batch phase a portion of 0.2% (w/v) mannose solution (16 g mannose in total) was added and exponential feeding of media I and II started with a ratio of 50:50 (interval I). On decrease of the slope the portion of mannose containing medium II was enhanced to 60% and the total feed F (media I and II) to 125% for maintaining growth based on glucose (interval II). After about 2 h again decrease of the slope was monitored and the portion of media II increased to 66.6% with simultaneous increase of the total feed F to 150% (interval III). After consumption of whole of media II fermentation was continued with feeding media I in a total feed of 100% (not shown in FIG. 10).

Progress and data of run 3 are summarized in the table 5 below:

TABLE 5

| interval [h] | medium I:II [%] | F [%] | µ [h$^{-1}$] | RFU | dry biomass [gDM/l] |
|---|---|---|---|---|---|
| 0-12 | | | 0.52 | — | |
| I 12-17 | 50:50 | 100 | 0.09 | 7000 | |
| II 17-19 | 50:75 | 125 | 0.08 | 9000 | |
| III 19-22 | 50:100 | 150 | 0.09 | 11000 | 22 |

In total 50 g mannose were added.

Each at 12 h, 20 h and 24 h a sample was taken for analysis of the expression on SDS-gel based on the soluble protein fractions of 10 OD$_{600}$ cells in total.

Figure 19:
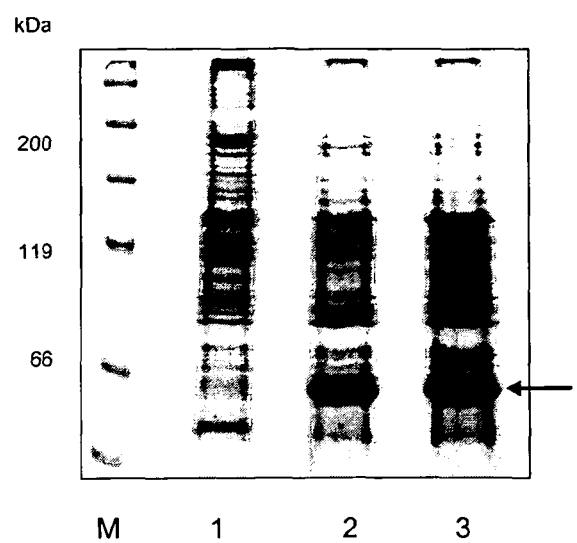
FIG. 19 a SDS page.

The resulting SDS page is shown in FIG. 19:

It is shown from the left: (M) length standard (ROTI®-Mark), (1) after 12 h, not induced; (2) after 20 h, 8 h-induction; (3) after 24 hours, 12 h induction.

After 20 h and 24 h a clear lane appears at about 27 kDa indicating expression of eGFP (arrow)

b) Fermentation Run 4

The same procedure as in run 3 was repeated except that the feed volume of medium II (mannose) was enhanced to 1.0 l in total.

Dry biomass concentration and the fluorescence signal are shown in FIGS. 14a and 12b, with the denotation being the same as in run 1. The progress and data are summarized in the table 6 below:

TABLE 6

| interval [h] | medium I:II [%] | F [%] | µ[h$^{-1}$] | RFU | dry biomass [gDM/l] |
|---|---|---|---|---|---|
| 0-15 | | | 0.40 | | |
| I 15-22 | 50:50 | 100 | | 3500 | |
| II 22-38 | 50:75 | 120 | | 10000-7800 | |
| III 38-39 | 50:100 | 150 | | 8900 | 40.4 |

In total 200 g mannose were added.

For compensating an observed lack of nitrogen after about 15 hours duration of fermentation (NH$_4$)$_2$HPO$_4$ was feeded additionally at a constant rate. In interval II a maximum RFU of 10000 was reached which within the course of interval II decreased to 7800 RFU.

a) Fermentation Runs 5 and 6: Without Impact Induction

Both fermentations were carried out in a 30 l fermentor.

In both runs the cells were grown until high cell density with exponentially increasing feed rate of glucose, which, upon reaching high cell density, was replaced by a constant feed of mannose.

The feed media I, II and III used are shown in the table 7 below:

TABLE 7

| Feed medium I | | Feed medium II | | Feed medium III | |
|---|---|---|---|---|---|
| Component | Concentration | Component | Concentration | component | Concentration |
| D-glucose*H$_2$O | 654.76 g/l | (NH$_4$)$_2$HPO$_4$ | 396.00 g/l | D-mannose | 400.00 g/l |
| MgSO$_4$*7H$_2$O | 23.50 g/l | | | MgSO$_4$*7H$_2$O | 23.50 g/l |
| TES | 120.00 ml/l | | | SEL | 120.00 ml/l |
| H$_2$O de-ionized | ad 4.2 l | H$_2$O de-ionized pH | ad 1.0 l 7.0 | H$_2$O de-ionized | ad 1.0 l |

Fermentation Run 5

Media I and II were added in proportion to their overall volumes 4.2:1.0 in exponentially increasing rate. On reaching high cell density feed composed of media I and II was replaced by feed composed of media II and III in a proportional ratio of 20:80 at constant volume corresponding to the volume of the last exponential feed rate of media I and II.

The fluorescence signal is shown in FIG. 15 with the denotation being the same as in run 1. It is assumed that the minimal increase of fluorescence signal in FIG. 15 after about 17 h fermentation duration was due to a short term leakage of medium III.

The progress and data of run 5 are summarized in the table 8 below:

TABLE 8

| Fed-batch phase [h] | Media [%] I:II:III | RFU max | Specific growth rate [h$^{-1}$] | Dry biomass [g DM/l] | mannose total [g] |
|---|---|---|---|---|---|
| 15-35 | 80.8:19.2:— | — | 0.1 | | |
| 35-39 | —:20:80 | 2,800 | | 80 | 150 | b) Fermentation Run 6

The same procedure as in run 5 was repeated except that in total 600 g mannose were added with an impact induction of 0.2 (w/v) mannose solution (16 g mannose in total) prior to the constant addition of feed composed of media II and III upon reaching high cell density. The fluorescence signal is shown in FIG. 16, with the denotation being the same as in run 1.

Progress and data of run 6 are summarized in table 9 below:

TABLE 9

| Fed-batch phase [h] | Media [%] I:II:III | RFU max | Specific growth rate [h$^{-1}$] | Dry biomass [g DM/l] | Mannose total [g] |
|---|---|---|---|---|---|
| 20-40 | 80.8:19.2:— | — | | | |
| 40 | 0.2% (w/v) Mannose solution | — | | | 16 |
| 42-53 | —:80:20 | 14000 | | 82 | 600 |

Evaluation of Runs 1 to 6

For evaluation at the time of maximal fluorescence the dry biomass concentration $c_x$, reactor volumes $V_R$, consumed mannose and duration from induction start were determined and summarized in table 10 below:

TABLE 10

| Fermentation run | Fluorescence$_{max}$ RFU | $c_x$ gDMl$^{-1}$ | VRI | Inducer gMan | Duration of expression h |
|---|---|---|---|---|---|
| 1 | 2200 | 16 | 8.2 | 16 | 5 |
| 2 | 4900 | 22 | 8.3 | 70 | 8 |
| 3 | 11000 | 22 | 1.6 | 50 | 10 |
| 4 | 10000 | 17 | 1.7 | 60 | 13 |
| 5 | 1700 | 80 | 12.0 | 150 | 5 |
| 6 | 14000 | 82 | 14.7 | 600 | 12 |

Based on the process data shown in table 10 for each run the productivity in terms of the maximal fluorescence RFU per liter and hour was calculated. Further, expression efficiency was expressed as relative fluorescence calculated from the maximal fluorescence based on absolute biomass (gDM) and the concentration of inductor (gman/L).

The results are shown in table 11 below:

TABLE 11

| Fermentation run | Productivity RFU l$^{-1}$ h$^{-1}$ | Rel. Fluorescence RFU(gDM)$^{-1}$ | Rel. fluorescence RFU (man/l)$^{-1}$ |
|---|---|---|---|
| 1 | 53.7 | 16.8 | 1127.5 |
| 2 | 73.8 | 26.8 | 581.0 |
| 3 | 687.5 | 312.5 | 352.0 |
| 4 | 452.5 | 346.0 | 283.3 |
| 5 | 28.3 | 1.8 | 136.0 |
| 6 | 79.4 | 11.6 | 343.0 |

These results clearly show that the present invention using plasmids carrying the mannose promoter can be successfully used in high cell density fermentation processes and positively controlled expression by addition of the inducer D-mannose.

Further, by selecting the induction regime the focus of the fermentation can be varied in maximizing output in view of biomass, expression product and inducer consumption, respectively, according to need.

In view of facilitated downstream processing inducer regime with combined impact induction and exponential feeding according to run 3 is particularly advantageous. Here, the high expression product generated relative to biomass makes further processing such as purification steps etc. more efficient and, thus, time- and cost-saving.

The invention claimed is:

1. Vector expressible in a prokaryotic host cell comprising a mannose-inducible promoter of the mannose operon of *Bacillus subtilis* operably linked to a transcriptional unit comprising a heterologous nucleic acid sequence encoding a polypeptide.

2. Vector according to claim 1 wherein the vector comprises the complete or a partial sequence of the regulatory gene manR.

3. Vector according to claim 1 wherein said promoter is the manP promoter.

4. Vector according to claim 3 wherein the manP promoter comprises a sequence selected from SEQ ID NO. 1 and SEQ ID NO. 2, a sequence complementary thereto or variants thereof.

5. Vector according to claim 1 wherein said promoter is the manR promoter.

6. Vector according to claim 5 wherein the manR promoter comprises a sequence selected from of SEQ ID NO. 3, SEQ ID NO. 4, and SEQ ID NO. 5, a sequence complementary thereto or variants thereof.

7. Vector according to claim 1 wherein the vector comprises upstream of the heterologous nucleic acid sequence a catabolite-responsive element.

8. Vector according to claim 1 wherein the vector comprises a transcription termination sequence located downstream from the heterologous nucleic acid sequence.

9. Vector according to claim 8 wherein the transcription termination sequence is that of the 3' region of the tufA gene of *Bacillus subtilis*.

10. Vector according to claim 1 wherein the vector is a shuttle vector replicable in *Escherichia coli* and *Bacillus subtilis*.

11. Vector according to claim 1 wherein the vector comprises at least one element selected from the group consisting of the replication origin of plasmid pUC 18 and/or the pBS72 replicon; or the rep gene of plasmid pUB 110 together with the replication origin of plasmid pUB 110.

12. Vector according to claim 1 wherein the heterologous nucleic acid sequence encodes an antibody or a fragment thereof.

13. Vector according to claim 3 comprising the transcription initiation region of manP gene.

14. Vector according to claim 5 wherein the transcription initiation region of manP gene or manR gene is replaced by the transcription initiation* region of another gene.

15. Vector according to claim 13 wherein the transcription initiation region of manP gene is replaced by the transcription initiation region of tufA gene gsiB gene or manR gene.

16. Vector according to claim 14 wherein the transcription initiation region of manP gene or manR gene is replaced by the transcription initiation region of tufA gene or gsiB gene.

17. Prokaryotic host cell transformed with the vector of claim 1.

18. Prokaryotic host cell according to claim 17 wherein the prokaryotic host cell is subject to carbon catabolite repression and comprises a phosphoenole pyruvate: carbohydrate phosphortransferase system.

19. Prokaryotic host cell according to claim 17 wherein the prokaryotic host cell is Gram-positive.

20. Prokaryotic host cell according to claim 17 wherein the host cell belongs to the phylum Firmicutes.

21. Method for producing a polypeptide in a prokaryotic host cell comprising the steps of constructing a vector according to claim 1 transforming a prokaryotic host cell with said vector, allowing expression of said polypeptide by growing the transformed host cell in a cell culture medium under suitable conditions and recovering the polypeptide from the cells or from the cell culture.

22. Method according to claim 21 wherein the host cells are grown first in the presence of a carbon source different from the inducer, and then, in a second step, in the presence of the inducer.

23. A method for using the vector of claim 1 for the regulated expression of a heterologous nucleic acid sequence encoding a polypeptide in a prokaryotic host cell, comprising the steps of:

transforming a prokaryotic host cell with said vector,
growing the transformed prokaryotic host cell in a culture medium under suitable conditions,
inducing expression of said polypeptide by addition of the inducer.

24. A method for using an isolated and purified nucleic acid sequence of the mannose-inducible promoter region of the mannose operon of *Bacillus subtilis*, a sequence complementary thereto or a variant thereof for the regulated expression of a heterologous nucleic acid sequence encoding a polypeptide in a prokaryotic host cell, comprising the steps of:

preparing an expression vector comprising that nucleic acid sequence, sequence complementary thereto or a variant thereof, which is operably linked to a transcriptional unit comprising a heterologous nucleic acid sequence encoding a polypeptide,
transforming a prokaryotic host cell with said vector,
growing the transformed prokaryotic host cell in culture medium under suitable conditions,
inducing expression of that polypeptide by addition of the inducer.

25. Vector according to claim 13 wherein the transcription initiation region of manP gene is replaced by the transcription initiation region of another gene.

* * * * *